US012080735B2

(12) United States Patent
Yagami

(10) Patent No.: US 12,080,735 B2
(45) Date of Patent: Sep. 3, 2024

(54) SOLID-STATE IMAGING ELEMENT, SOLID-STATE IMAGING DEVICE, AND ELECTRONIC EQUIPMENT

(71) Applicant: Sony Semiconductor Solutions Corporation, Kanagawa (JP)

(72) Inventor: Takanori Yagami, Kanagawa (JP)

(73) Assignee: Sony Semiconductor Solutions Corporation, Kanagawa (JP)

( * ) Notice: Subject to any disclaimer, the term of this patent is extended or adjusted under 35 U.S.C. 154(b) by 612 days.

(21) Appl. No.: 17/291,206

(22) PCT Filed: Nov. 6, 2019

(86) PCT No.: PCT/JP2019/043566
§ 371 (c)(1),
(2) Date: May 4, 2021

(87) PCT Pub. No.: WO2020/100697
PCT Pub. Date: May 22, 2020

(65) Prior Publication Data
US 2021/0358982 A1    Nov. 18, 2021

(30) Foreign Application Priority Data

Nov. 13, 2018  (JP) ................................ 2018-213051

(51) Int. Cl.
*H01L 27/146*  (2006.01)
*H04N 25/70*  (2023.01)
(Continued)

(52) U.S. Cl.
CPC .................. *H01L 27/14612* (2013.01); *H01L 27/14643* (2013.01); *H04N 25/70* (2023.01); *A61B 1/05* (2013.01); *B60R 11/04* (2013.01)

(58) Field of Classification Search
CPC .......... H01L 27/14612; H01L 27/14643; H03F 3/45

See application file for complete search history.

(56) References Cited

U.S. PATENT DOCUMENTS

| 2012/0081180 | A1* | 4/2012 | Lee | G06F 30/39 716/120 |
| 2017/0272678 | A1* | 9/2017 | Sakakibara | H04N 25/75 |
| 2020/0280694 | A1* | 9/2020 | Morita | H04N 25/75 |

FOREIGN PATENT DOCUMENTS

| CN | 103379292 A | 10/2013 |
| CN | 105519096 A | 4/2016 |

(Continued)

OTHER PUBLICATIONS

International Search Report (PCT/ISA/210), International Application No. PCT/JP2019/043566, dated Jan. 30, 2020.

(Continued)

*Primary Examiner* — Thanh Luu
(74) *Attorney, Agent, or Firm* — Michael Best & Friedrich LLP

(57) ABSTRACT

A solid-state imaging element (1) includes a pixel circuit (20) in which a first transistor (26) that amplifies a pixel signal is arranged, the pixel signal being generated by a photoelectric converter performing photoelectric conversion on light that has entered a pixel. The pixel circuit (20) includes a second transistor (27) into which a reference signal is input from a reference signal generator, and a third transistor (28) that outputs bias current to the first transistor (26) and the second transistor (27).

21 Claims, 20 Drawing Sheets

(51) Int. Cl.
　　　*A61B 1/05*　　　(2006.01)
　　　*B60R 11/04*　　　(2006.01)

(56) References Cited

FOREIGN PATENT DOCUMENTS

| | | |
|---|---|---|
| CN | 106899814 A | 6/2017 |
| CN | 107615487 A | 1/2018 |
| JP | 2012114838 A | 6/2012 |
| TW | 201644265 A | 12/2016 |
| TW | 201826515 A | 7/2018 |
| WO | 2016009832 A1 | 1/2016 |
| WO | 2016194653 A1 | 12/2016 |

OTHER PUBLICATIONS

Notification of Transmittal of the International Search Report and the Written Opinion of the International Searching Authority, or the Declaration (PCT/ISA/220), International Application No. PCT/JP2019/043566, dated Feb. 10, 2020.
Written Opinion of the International Search Authority (PCT/ISA/237), International Application No. PCT/JP2019/043566, dated Feb. 10, 2020.

\* cited by examiner

SOLID-STATE IMAGING ELEMENT, SOLID-STATE IMAGING DEVICE, AND ELECTRONIC EQUIPMENT

TECHNICAL FIELD

The present disclosure relates to a solid-state imaging element, a solid-state imaging device, and electronic equipment.

BACKGROUND ART

In order to achieve downsizing and improve a pixel aperture ratio, imaging devices configured by laminating a pixel substrate on which pixels are arranged and a logic substrate on which peripheral circuits are mounted are known.

For example, proposed is an imaging device in which pixels are arranged in a two-dimensional lattice on a pixel substrate and an analog-to-digital converter for processing a pixel signal output from a pixel is arranged on a logic substrate (for example, PTL 1).

CITATION LIST

Patent Literature

[PTL 1]
WO 2016/009832

SUMMARY

Technical Problem

In the above related art, however, since the pixels and the analog-to-digital converter are arranged on different substrates, wiring for connecting the pixels and the analog-to-digital converter becomes longer. The signal level of an analog pixel signal is relatively weak. Hence, the analog pixel signal is liable to be affected by noise when the signal is being transmitted on the wiring. Therefore, a technology capable of reducing the influence of noise is demanded.

Accordingly, the present disclosure proposes a solid-state imaging element, a solid-state imaging device, and electronic equipment which are capable of reducing the influence of noise.

Solution to Problem

In order to address the above drawback, a solid-state imaging element according to one aspect of the present disclosure includes a pixel circuit in which a first transistor that amplifies a pixel signal is arranged, the pixel signal being generated by a photoelectric converter performing photoelectric conversion on light that has entered a pixel, the pixel circuit including a second transistor into which a reference signal is input from a reference signal generator, and a third transistor that outputs bias current to the first transistor and the second transistor.

DESCRIPTION OF EMBODIMENTS

Hereinafter, embodiments of the present disclosure will be described with reference to the accompanying drawings. It is to be noted that is each of the embodiments below, identical parts are applied with identical reference signs and overlapping descriptions will be omitted.

Figure 1:
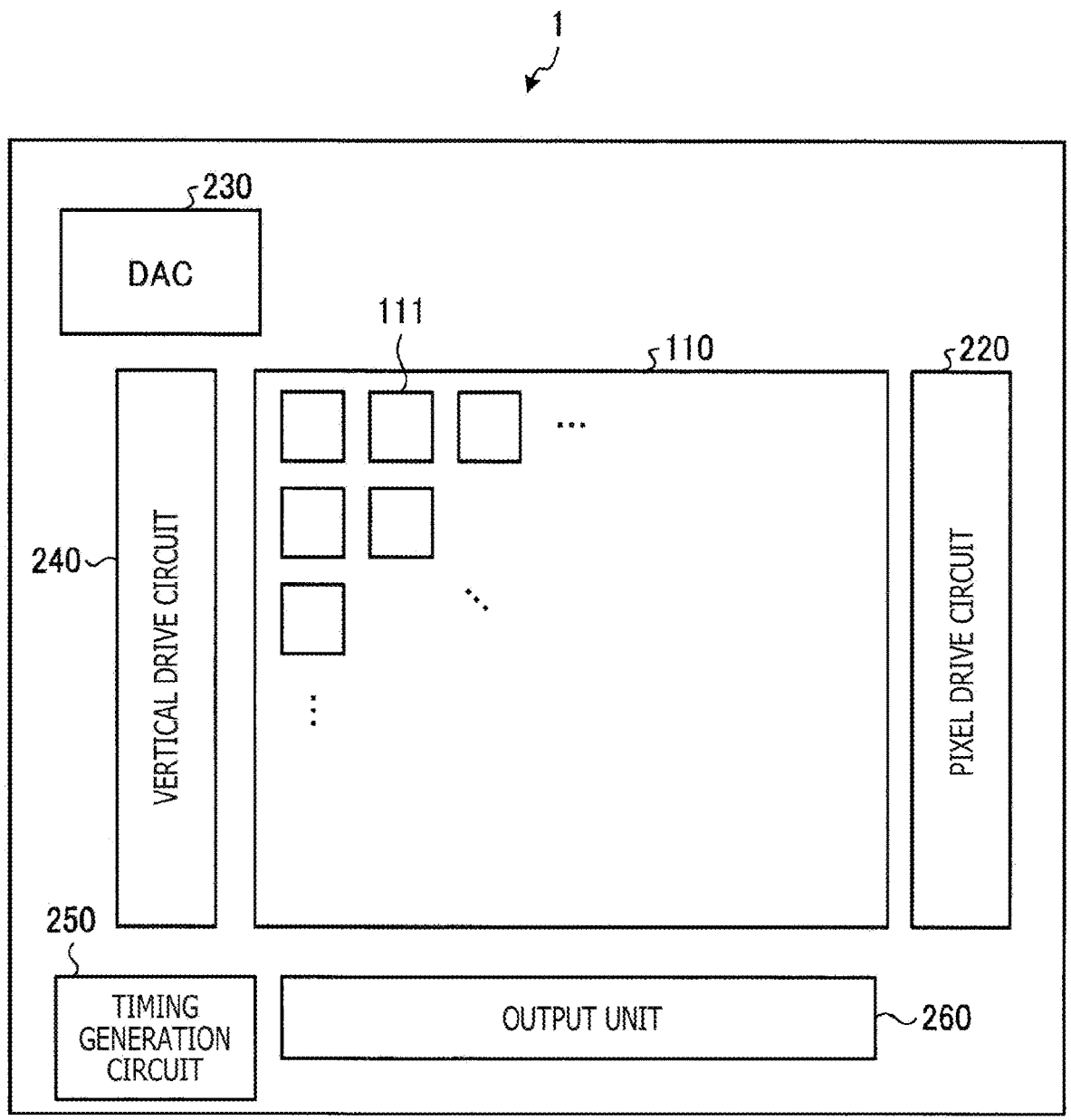
FIG. 1 is a block diagram depicting an example of components of a solid-state imaging element according to an embodiment of the present disclosure.

In addition, the present disclosure will be described according to the order of items listed below.
1. Embodiment
   1-1. Configuration of Solid-State Imaging Element
   1-2. Laminated Structure of Solid-State Imaging Element
   1-3. Configuration of Pixel Circuit
2. First Modification
3. Second Modification
4. Third Modification
5. Fourth Modification
6. Fifth Modification
7. Sixth. Modification
8. Application Example to Solid-State Imaging Device
9. Application Example to Endoscopic Surgery System
10. Application Example to Mobile Body 1. Embodiment 1-1. Configuration of Solid-State Imaging Element Referring to FIG. 1, components of a solid-state imaging element according to an embodiment of the present disclosure will be described. FIG. 1 is a block diagram depicting an example of the components of the solid-state imaging element according to an embodiment of the present disclosure. The solid-state imaging element according to an embodiment of the present disclosure can be applied to various types of electronic equipment on which a digital camera or the like is mounted.

As depicted in FIG. 1, a solid-state imaging element 1 includes a pixel array unit 110, a pixel drive circuit 220, a DAC 230, a vertical drive circuit 240, a timing generation circuit 250, and an output unit 260.

A plurality of pixels 111 is arranged in a two-dimensional array in the pixel array unit 110. A configuration of the pixel 111 will be described later.

Figure 3:
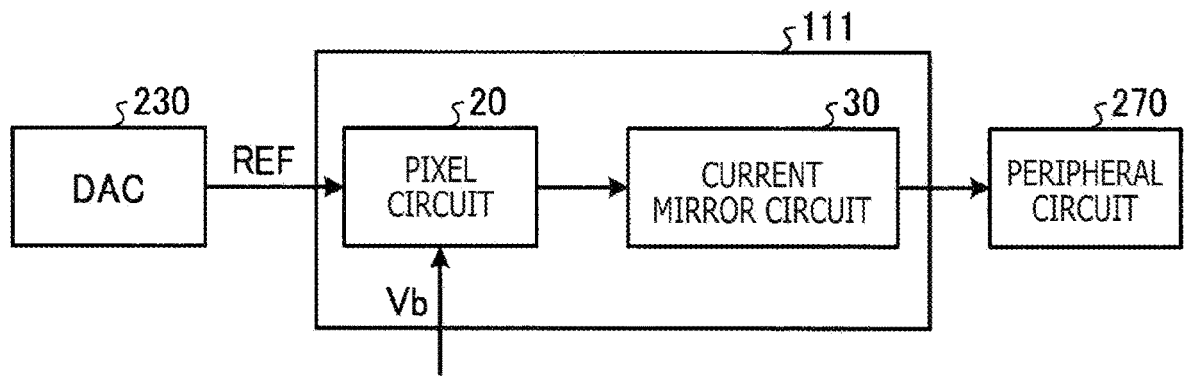
FIG. 3 is a schematic diagram depicting a configuration of a pixel according to an embodiment of the present disclosure.

The pixel drive circuit 220, for example, drives a pixel circuit depicted in FIG. 3, in the pixel 111.

The DAC 230, for example, generates a reference signal REF, a voltage of which monotonously decreases according to the lapse of time. The DAC 230, for example, outputs the reference signal REF that has been generated to the pixel 111.

The vertical drive circuit 240, for example, conducts control for outputting a digital pixel signal that has been generated in the pixel 111 to the output unit 260 in a predetermined order, on the basis of a timing signal supplied from the timing generation circuit 250.

The timing generation circuit 250, for example, generates various kinds of timing signals. The timing generation circuit 250, for example, outputs the various kinds of timing signals that have been generated to the pixel drive circuit 220, the DAC 230, the vertical drive circuit 240, or the like.

1-2. Laminated Structure of Solid-State Imaging Element

Figure 2:
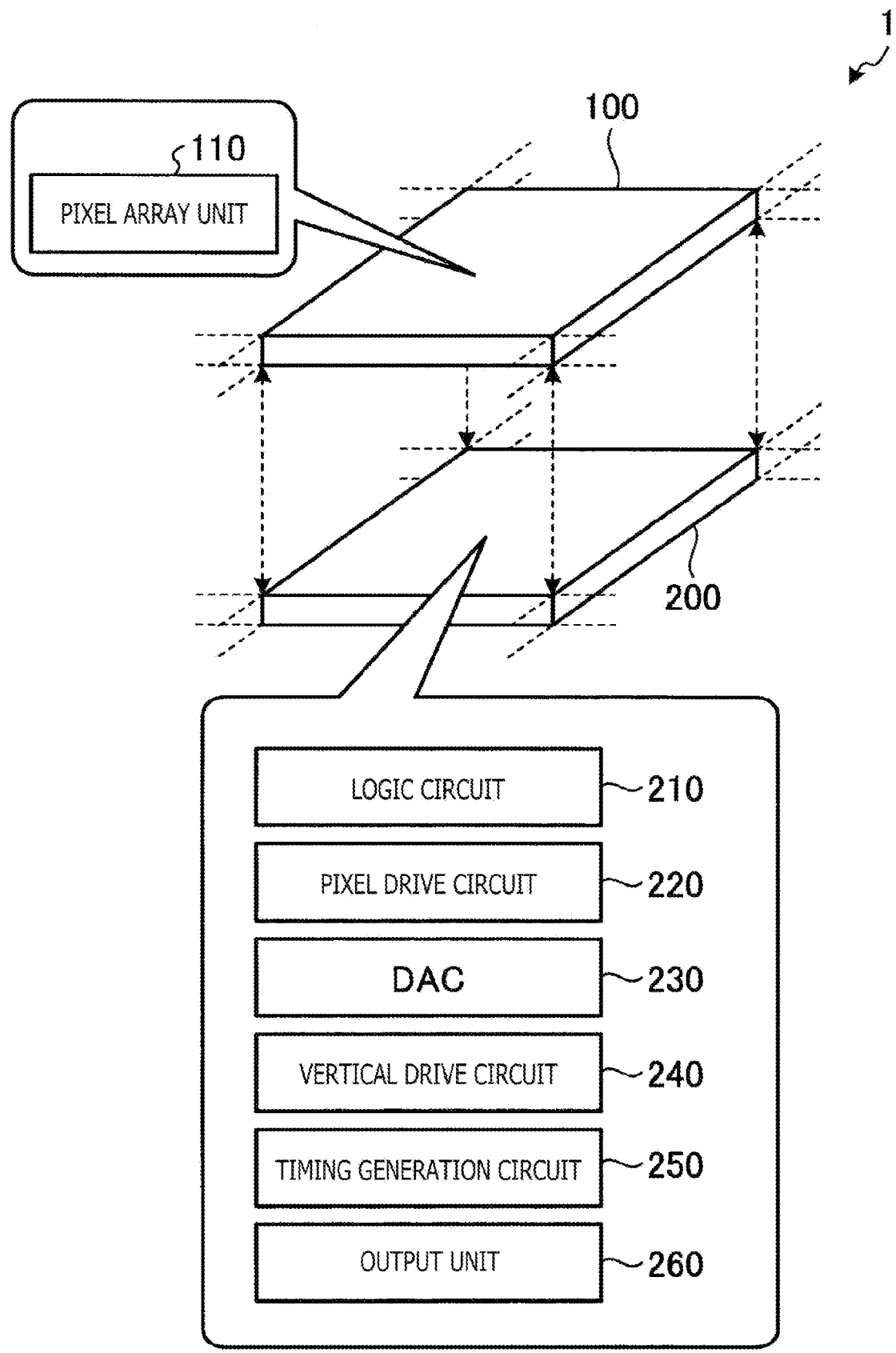
FIG. 2 is a schematic diagram for describing a laminated structure of the solid-state imaging element according to an embodiment of the present disclosure.

Referring to FIG. 2, a laminated structure of the solid-state imaging element according to an embodiment of the present disclosure will be described. FIG. 2 is a schematic diagram for describing a laminated structure of the solid-state imaging element according to an embodiment of the present disclosure.

As depicted in FIG. 2, the solid-state imaging element 1 has a structure in which a first substrate 100 and a second substrate 200 are laminated. The solid-state imaging element 1 includes, for example, the pixel array unit 110, a logic circuit 210, the pixel drive circuit 220, the DAC (Digital to Analog Converter) 230, the vertical drive circuit 240, the timing generation circuit 250, and the output unit 260.

The first substrate 100 and the second substrate 200 may be bonded together, for example, in a generally-called CoC (Chip on Chip) method in which the first substrate 100 and the second substrate 200 are respectively singulated into chips and then the first substrate 100 and the second substrate 200 which have been singulated are bonded together. In addition, the first substrate 100 and the second substrate 200 may be bonded in a generally-called CoW (Chip on Wafer) method in which either of the first substrate 100 or the second substrate 200 (for example, the first substrate 100) is singulated into chips and then the first substrate 100 which has been singulated may be bonded to the second substrate 200 before being singulated (that is, in a wafer state). Further, the first substrate 100 and the second substrate 200 both is a wafer state may be bonded together in a generally-called WoW (Wafer on Wafer) method.

For example, plasma bonding or the like can be used for the bonding method for bonding the first substrate 100 and the second substrate 200. However, various bonding methods may be used without being limited to the above methods.

The sines of the first substrate 100 and the second substrate 200 may be the same or may be different. The first substrate 100 and the second substrate 200 are each, for example, a semiconductor substrate such as a silicon substrate.

For example, the pixel array unit 110 is arranged on the first substrate 100.

The second substrate 200 includes, for example, the logic circuit 210, the pixel drive circuit 220, the DAC 230, the vertical drive circuit 240, the timing generation circuit 250, and the output unit 260.

Referring to FIG. 3, the pixel according to the present embodiment will be described. FIG. 3 is a block diagram depicting a configuration of the pixel 111 according to the present embodiment.

As illustrated in FIG. 3, the pixel ill includes a pixel circuit 20 and a current mirror circuit 30.

The pixel circuit 20, as will be described later in detail, includes, for example, a photoelectric converter for generating and accumulating an electric charge signal corresponding to a light quantity of a received light, and generates an analog pixel signal. In addition, the pixel circuit 20, for example, has a function of converting the analog pixel signal that has been generated into a digital pixel signal. That is, the pixel circuit 20 converts the analog image signal that has been Generated into a digital image signal by itself. Specifically, the pixel circuit 20 includes a transistor into which the reference signal REF is input from the DAC 230, and a transistor into which bias current is input.

The current mirror circuit 30 outputs a predetermined signal to a peripheral circuit 270, in a case where a pixel signal SIG is greater than the reference signal REF.

1-3. Configuration of Pixel Circuit

Figure 4:
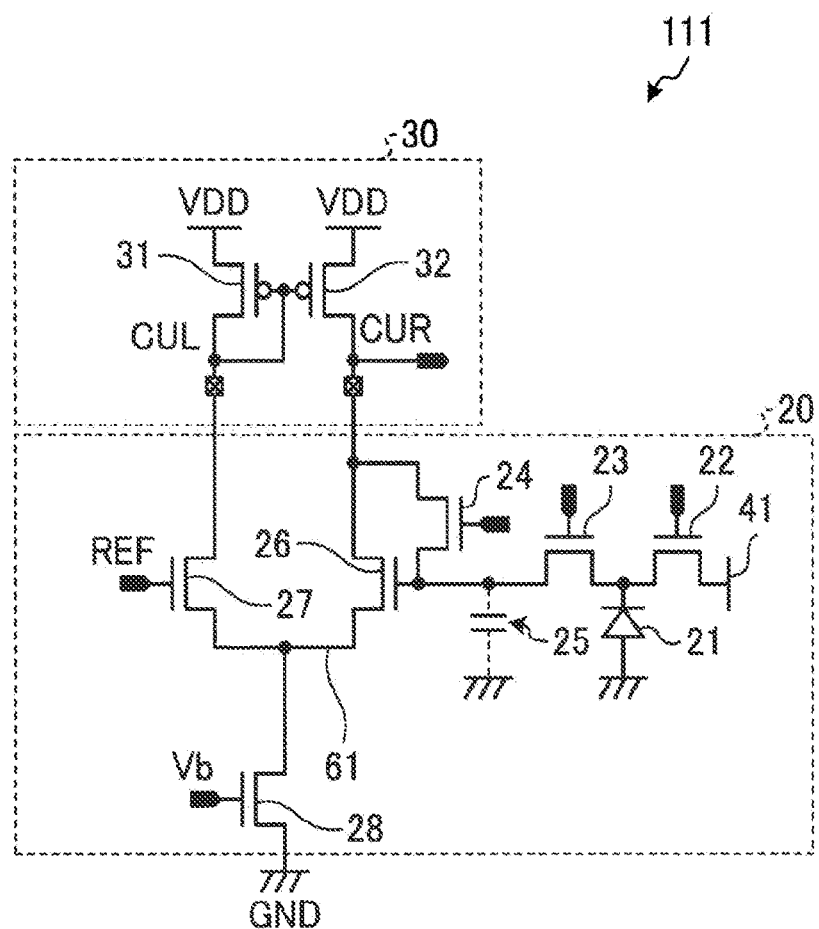
FIG. 4 is a circuit diagram depicting a configuration of a pixel circuit according to an embodiment of the present disclosure.

Referring to FIG. 4, a configuration of a pixel circuit according to an embodiment of the present disclosure will be described. FIG. 4 is a circuit diagram depicting a configuration of the pixel circuit according to an embodiment of the present disclosure.

As illustrated in FIG. 4, the pixel circuit 20 includes a photoelectric converter 21, a discharge transistor 22, a transfer transistor 23, a reset transistor 24, a floating diffusion layer (FD) 25, an amplification transistor 26, a reference transistor 27, and a bias transistor 28. That is, in the present embodiment, the amplification transistor 26, the reference transistor 27, and the bias transistor 28 are arranged inside the pixel circuit 20. In other words, in the present embodiment, the current source of a reference signal and the current source of bias current are arranged inside the pixel circuit 20.

The current mirror circuit 30 includes a transistor 31 and a transistor 32. The transistor 31 and the transistor 32 each include, for example, a PMOS transistor.

The photoelectric converter 21, for example, receives light, performs photoelectric conversion, and generates an electric charge corresponding to the light quantity of the received light. The photoelectric converter 21 can be realized by, for example, a photodiode.

The discharge transistor 22 is used in adjusting an exposure period. Specifically, in a case where the discharge transistor is turned on at an optional timing when the exposure period is desired to be started, the electric charge accumulated in the photoelectric converter 21 until that time is discharged to as overflow drain 41. Therefore, after the discharge transistor 22 is turned off next, the exposure period is started.

The transfer transistor 23 transfers the electric charge that has been generated by the photoelectric converter 21 to the floating diffusion layer 25.

The reset transistor 24 resets the charge held in the floating diffusion layer 25.

A gate of the amplification transistor 26 is connected with the floating diffusion layer 25. Therefore, the amplification transistor 26 amplifies a charge signal output from the floating diffusion layer 25. A source of the amplification transistor 26 is connected with a drain of the bias transistor 28. The source of the amplification transistor and the drain of the bias transistor 28 are connected with each other through routing wiring 61. A drain of the amplification transistor 26 is connected with a drain of the transistor 32.

The reference transistor 27, together with the amplification transistor 26, constitutes a differential pair. That is, a part of the differential amplifier is provided in the pixel circuit 20. Specifically, the amplification transistor 26, the reference transistor 27, the bias transistor 28, and the current mirror circuit 30 function as a differential amplifier. The reference signal REF that has bees output from the DAC 230 is input into a gate of the reference transistor 27. A source of the reference transistor 27 is connected with the drain of the bias transistor 28. Here, the source of the reference transistor 27 and the drain of the bias transistor 28 are connected with each other through the routing wiring 61. A drain of the reference transistor 27 is connected with gates of the transistor 31 and the transistor 32. In addition, the drain of the reference transistor 27 is connected with a drain of the transistor 31.

A gate of the bias transistor 28 is connected with a current source, not illustrated. In addition, a current signal is output from the current source to the gate of the bias transistor 28. A source of the bias transistor 28 is connected to a GND. Therefore, the bias transistor 28 outputs bias current Vb to the amplification transistor 26 and the reference transistor 27.

As described above, the pixel circuit 20 includes the amplification transistor 26, the reference transistor 27, and the bias transistor 28. Therefore, an analog pixel signal can be converted into a digital pixel signal in the inside of the pixel circuit 20. Accordingly, the routing wiring 61 for connecting the amplification transistor 26, the reference transistor 27, and the bias transistor 28 can be shortened. Consequently, the influence of noise can be reduced.

Figure 5:
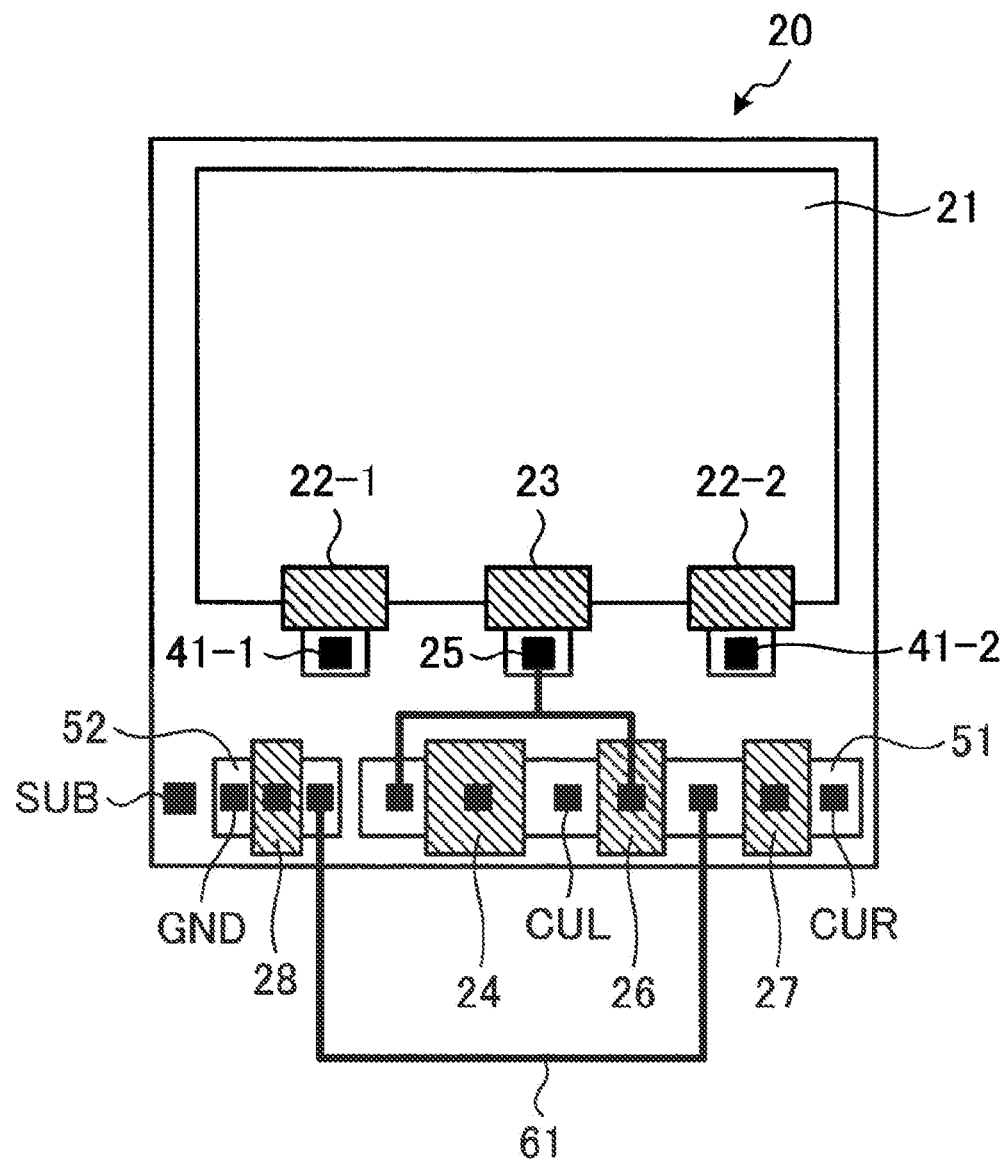
FIG. 5 is a schematic diagram depicting an example of an arrangement of transistors in a pixel according to an embodiment of the present disclosure.

Referring to FIG. 5, an example of an arrangement of each transistor in the pixel circuit 20 will be described. FIG. 5 is a schematic diagram depicting an example of an arrangement of each transistor according to an embodiment of the present disclosure.

A first discharge transistor 21-1, a second discharge transistor 21-2, and the transfer transistor 23 are connected with the photoelectric converter 21. In this case, the first discharge transistor 21-1 discharges the electric charge accumulated is the photoelectric converter 21 to a first overflow drain 41-1. Specifically, the first discharge transistor 21-1 discharges the electric charge accumulated in the first discharge transistor 21-1 rather than in the second discharge transistor 21-2, in the photoelectric converter 21. The second discharge transistor 21-2 discharges the electric charge accumulated in the photoelectric converter 21 to a second overflow drain 41-2. Specifically, the second discharge transistor 21-2 discharges the electric charge accumulated is the second discharge transistor 21-2 rather than the first discharge transistor 21-1, in the photoelectric converter 21. In this manner, by connecting the two discharge transistors with the photoelectric converter 21, the electric charge accumulated in the photoelectric converter 21 can be efficiently discharged.

The two transistors of the first discharge transistor 21-1 and the second discharge transistor 21-2 are connected with the photoelectric converter 21. However, this is an illustrative example and does not limit the present disclosure. The number of the discharge transistors connected with the photoelectric converter 21 may be one or three or more. That is, at least one discharge transistor may be connected with the photoelectric converter 21. In addition, in a case where a plurality of discharge transistors is connected with the photoelectric converter 21, the plurality of discharge transistors may be connected on the same side or may be connected on different sides.

The transfer transistor 23 transfers the electric charge that has been generated by the photoelectric converter 21 to the floating diffusion layer 25, as described above. The floating diffusion layer 25 is connected with a ground pad GNP and the amplification transistor 26. The ground is determined by a SUB pad in the pixel circuit 20.

The reset transistor 24, the amplification transistor 26, and the reference transistor 27 are linearly arranged. The reset transistor 24, the amplification transistor 26, and the reference transistor 27 are electrically connected with one another through a first diffusion layer 51. A terminal CUL and a terminal CUR are terminals for outputting output signals from the amplification transistor 26 and the reference transistor 27 to a peripheral circuit.

The bias transistor 28 is electrically connected with a second diffusion layer 52 which is different from the first diffusion layer 51. Here, the first diffusion layer 51 and the second diffusion layer 52 are not electrically connected. Therefore, the bias transistor 28, the amplification transistor 26, and the reference transistor 27 are electrically connected with one another through the routing wiring 61.

As described above, in the present embodiment, the reference transistor 27 and the bias transistor 28 are arranged in the pixel circuit 20, and the amplification transistor 26, the reference transistor 27, and the bias transistor 28 are electrically connected with one another through the routing wiring 61. Thus, the length of the routing wiring can be shortened as compared with a case where the bias transistor 28 functioning as a constant current source is arranged outside the pixel circuit 20. Consequently, the influence of noise is reduced.

Figure 6:
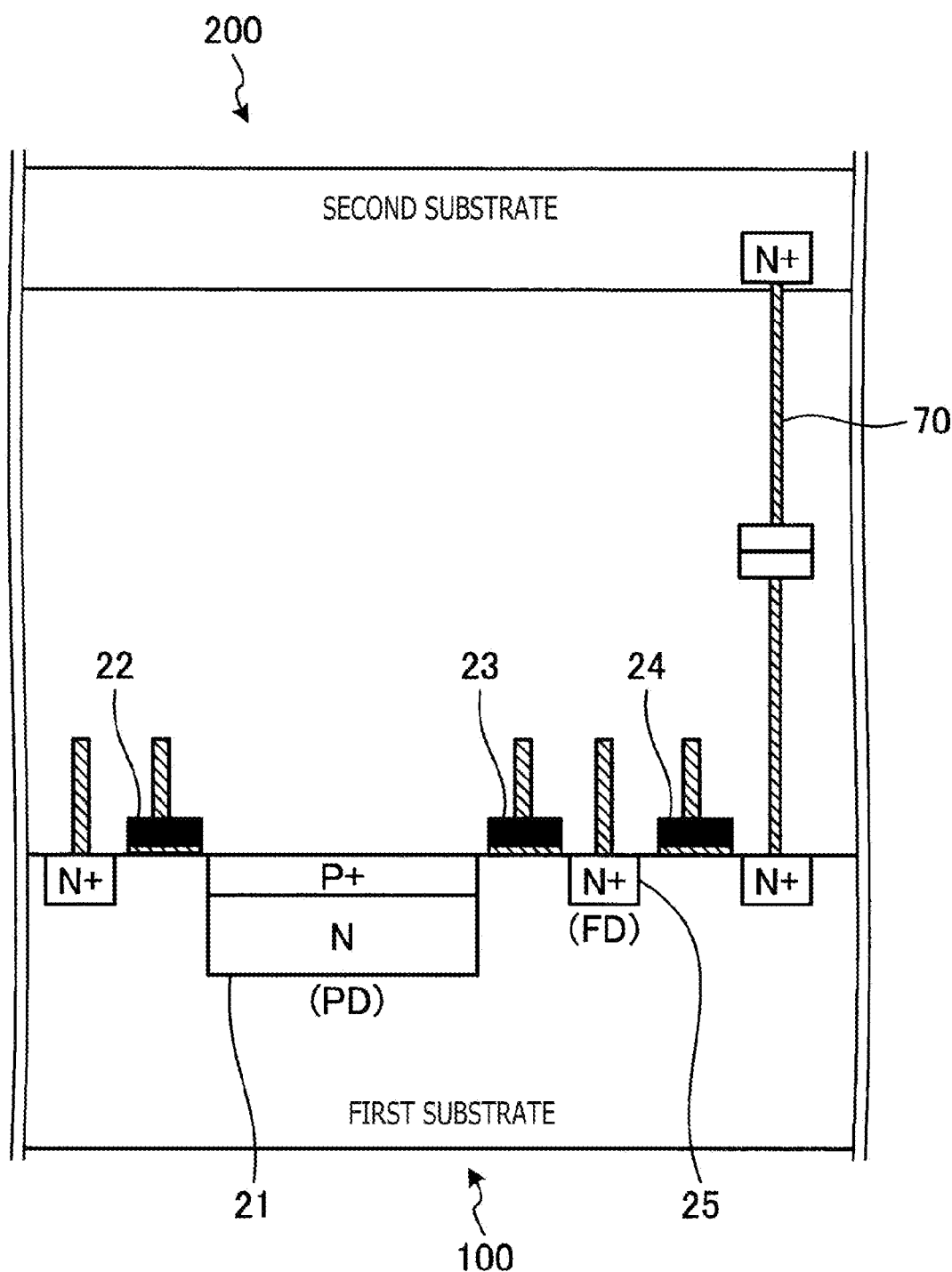
FIG. 6 is a schematic diagram depicting an example of a configuration in cross section of a pixel according to an embodiment of the present disclosure.

FIG. 6 is a schematic diagram depicting a configuration in cross section of a pixel according to an embodiment. The photoelectric converter 21, the discharge transistor 22, the transfer transistor 23, the reset transistor 24, and the floating diffusion layer 25 which are formed in the first substrate are depicted in FIG. 6. In a left part of the discharge transistor 22, an N+ layer doped with a relatively large amount of donor is formed. The photoelectric converter 21 is provided between the discharge transistor 22 and the transfer transistor 23 and is configured by laminating a P+ layer on an upper part of an N-type semiconductor. The floating diffusion layer 25 includes an N+ layer. In addition, the first substrate 100 and the second substrate 200 are connected with each other through connection wiring 70, which is provided so as to connect the respective N+ layers formed in the first substrate 100 and the second substrate 200.

2. First Modification

Figure 7:
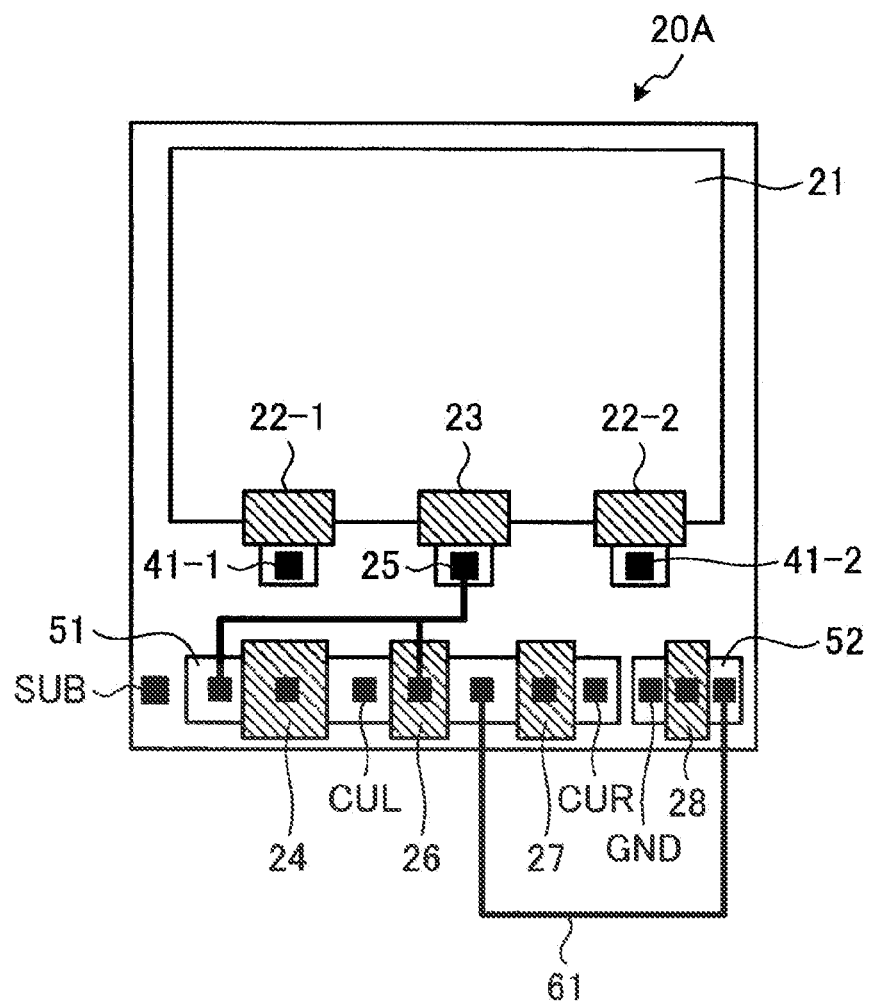
FIG. 7 is a schematic diagram depicting an example of an arrangement of transistors in a pixel according to a first modification of the embodiment of the present disclosure.

Referring to FIG. 7, an arrangement of transistors in a pixel according to a first modification of the present embodiment will be described. FIG. 7 is a schematic diagram depicting the arrangement of the transistors in the pixel according to the first modification of the present embodiment.

As depicted in FIG. 7, the reset transistor 24, the amplification transistor 26, and the reference transistor 27 are linearly arranged. The reset transistor 24, the amplification transistor 26, and the reference transistor 27 are electrically connected with one another through the first diffusion layer 51. The bias transistor 28 is electrically connected with the second diffusion layer 52 which is different from the first diffusion layer 51.

Here, in a pixel circuit 20A, the amplification transistor 26, the reference transistor 27, and the bias transistor 28 are arranged in this order along the first diffusion layer 51. Accordingly, the length of the routing wiring 61 for electrically connecting the amplification transistor 26, the reference transistor 27, and the bias transistor 28 can be made shorter. Consequently, the influence of noise can be further reduced.

In the first modification, it is preferable that the source of the reference transistor 27 and a ground node to which the drain of the bias transistor 28 is connected are adjacent to each other. The dark current can be reduced by making the source of the reference transistor 27 adjacent to the ground.

3. Second Modification

Figure 8:
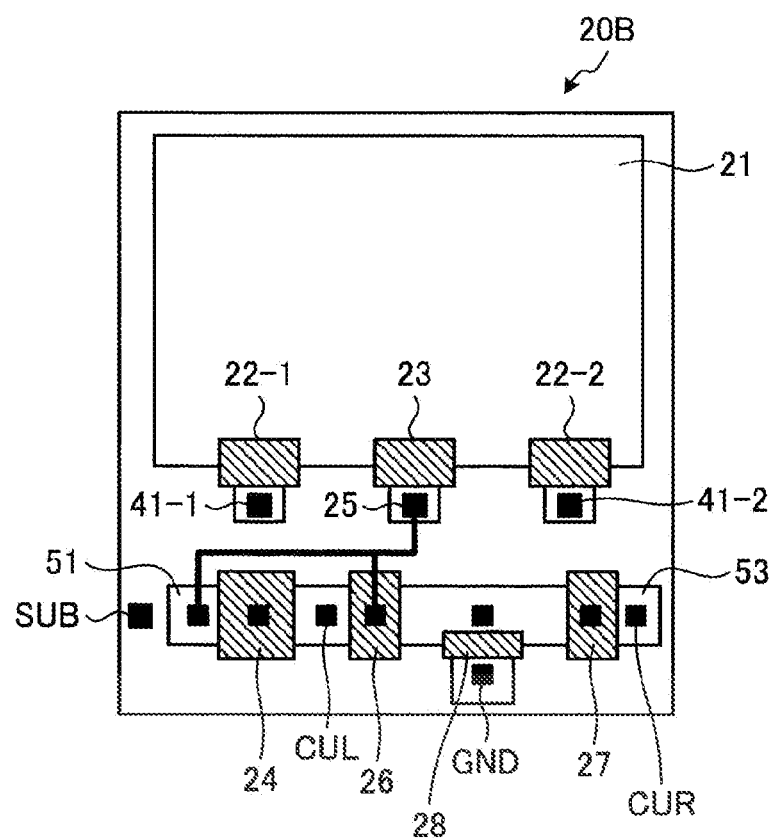
FIG. 8 is a schematic diagram depicting an example of an arrangement of transistors in a pixel according to a second modification of the embodiment of the present disclosure.

Referring to FIG. 8, an arrangement of transistors in a pixel according to a second modification of the present embodiment will be described. FIG. 8 is a schematic diagram depicting the arrangement of the transistors in the pixel according to the second modification of the present embodiment.

As depicted in FIG. 8, the reset transistor 24, the amplification transistor 26, the reference transistor 27, and the bias transistor 28 are electrically connected with one another through an identical third diffusion layer 53. That is, the reset transistor 24, the amplification transistor 26, the reference transistor 27, and the bias transistor 28 share the diffusion layer. Specifically, the drain of the bias transistor 28 is connected with the third diffusion layer. Therefore, in the second modification, there is no need to provide the routing wiring 61 for electrically connecting the amplification transistor 26, the reference transistor 27, and the bias transistor 28. Consequently, in the second modification, for example, the cost can be reduced. In addition, since no consideration is given to the routing pattern of the routing wiring 61, the design is facilitated.

4. Third Modification

Figure 9:
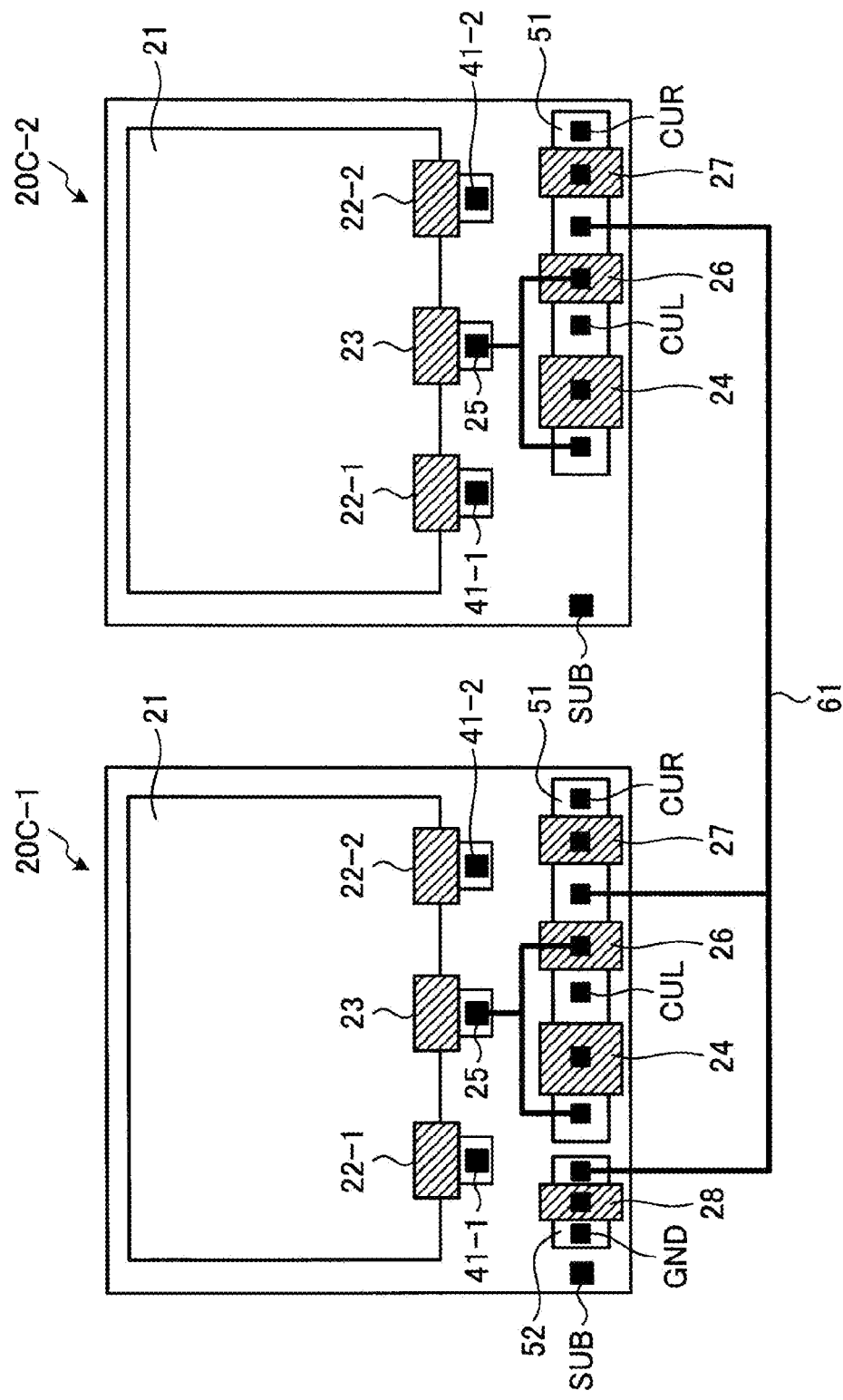
FIG. 9 is a schematic diagram depicting an example of an arrangement of transistors in a pixel according to a third modification of the embodiment of the present disclosure.

Referring to FIG. 9, an arrangement of transistors in a pixel according to a third modification of the present embodiment will be described. FIG. 9 is a schematic diagram depicting the arrangement of the transistors is the pixel according to the third modification of the present embodiment.

A first pixel circuit 20C-1 and a second pixel circuit 20C-2 are depicted in FIG. 9. The first pixel circuit 20C-1 has a configuration similar to that of the pixel circuit 20 illustrated in FIG. 5. The second pixel circuit 20C-2 is different from the pixel circuit 20 illustrated in FIG. 5 in that the bias transistor 28 is not provided.

As depicted in FIG. 9, the first pixel circuit 20C-1 and the second pixel circuit 20C-2 share the bias transistor 28 provided in the first pixel circuit 20C-1. Specifically, the second pixel circuit 20C-2 and the bias transistor 28 are connected with each other through the routing wiring 61 which is provided between the first pixel circuit 20C-1 and the second pixel circuit 20C-2. In this case, the bias transistor 28 outputs bias current to the amplification transistor 26 and the reference transistor 27 in each of the first pixel circuit 20C-1 and the second pixel circuit 20C-2. Accordingly, the number of the bias transistors 28 to be used in the entire solid-state imaging element can be reduced. Consequently, the cost can be reduced.

It is to be noted that in FIG. 9, a configuration in which the bias transistor is shared between two pixel circuits has been described. However, this is an illustrative example and does not limit the present disclosure. In the present disclosure, a bias transistor may be shared among three or more pixel circuits. In this case, for example, the routing wiring may be provided for connecting a plurality of pixels. Further, in the present disclosure, a plurality of pixel circuits including a bias transistor and a plurality of pixel circuits not including a bias transistor may be combined.

5. Fourth Modification

Figure 10:
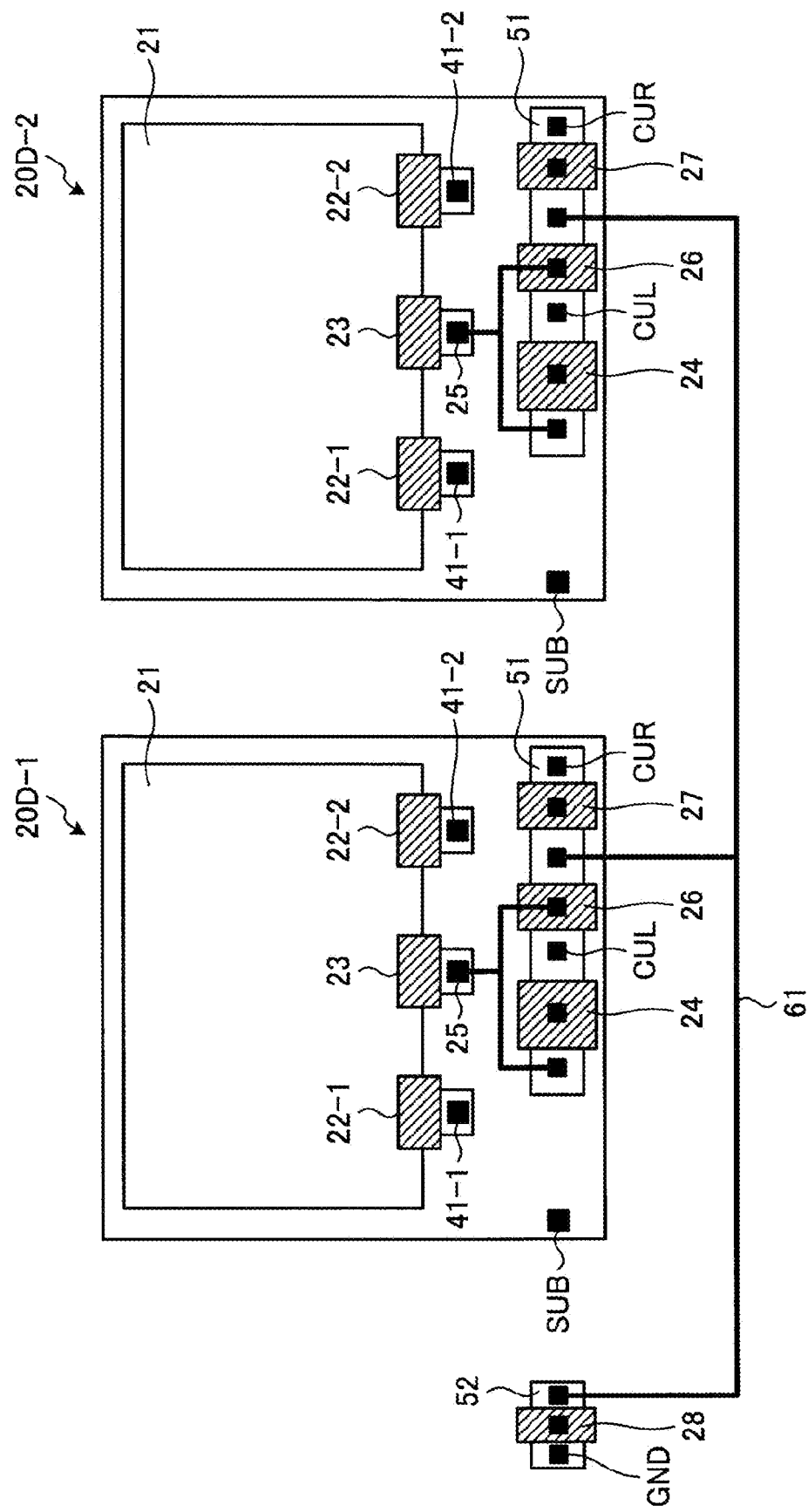
FIG. 10 is a schematic diagram depicting an example of an arrangement of transistors in a pixel according to a fourth modification of the embodiment of the present disclosure.

Referring to FIG. 10, an arrangement of transistors in a pixel according to a fourth modification of the present embodiment will be described. FIG. 10 is a schematic diagram depicting the arrangement of the transistors in the pixel according to the fourth modification of the present embodiment.

In FIG. 10, a first pixel circuit 20D-1 and a second pixel circuit 20D-2 are different from the pixel circuit 20 depicted in FIG. 5 in that the bias transistor 28 is not provided.

In the fourth modification, the bias transistor 28, for example, is mounted on a peripheral circuit of the pixel array unit. That is, in the fourth modification, the amplification transistor 26 and the reference transistor 27 are arranged in each of the first pixel circuit 20D-1 and the second pixel circuit 20D-2, but the bias transistor 28 is arranged outside.

The first pixel circuit 20D-1 and the second pixel circuit 20D-2 share the bias transistor 28 arranged outside. Specifically, the first pixel circuit 20D-1 and the second pixel circuit 20D-2 are electrically connected with the bias transistor 28 through, for example, the routing wiring 61. In this case, the bias transistor 28 inputs bias current into the amplification transistor 26 and the reference transistor 27 in each of the first pixel circuit 20D-1 and the second pixel circuit 20D-2. Accordingly, the number of the bias transistors 28 to be used in the entire solid-state imaging element can be reduced. Consequently, the cost can be reduced.

It is to be noted that, in FIG. 10, the bias transistor 28 shared between pixel circuits in an identical substrate has been described. However, this is an illustrative example and does not limit the present disclosure. In the present disclosure, for example, the bias transistor 28 may be shared between the pixel circuits arranged on different substrates.

Figure 11:
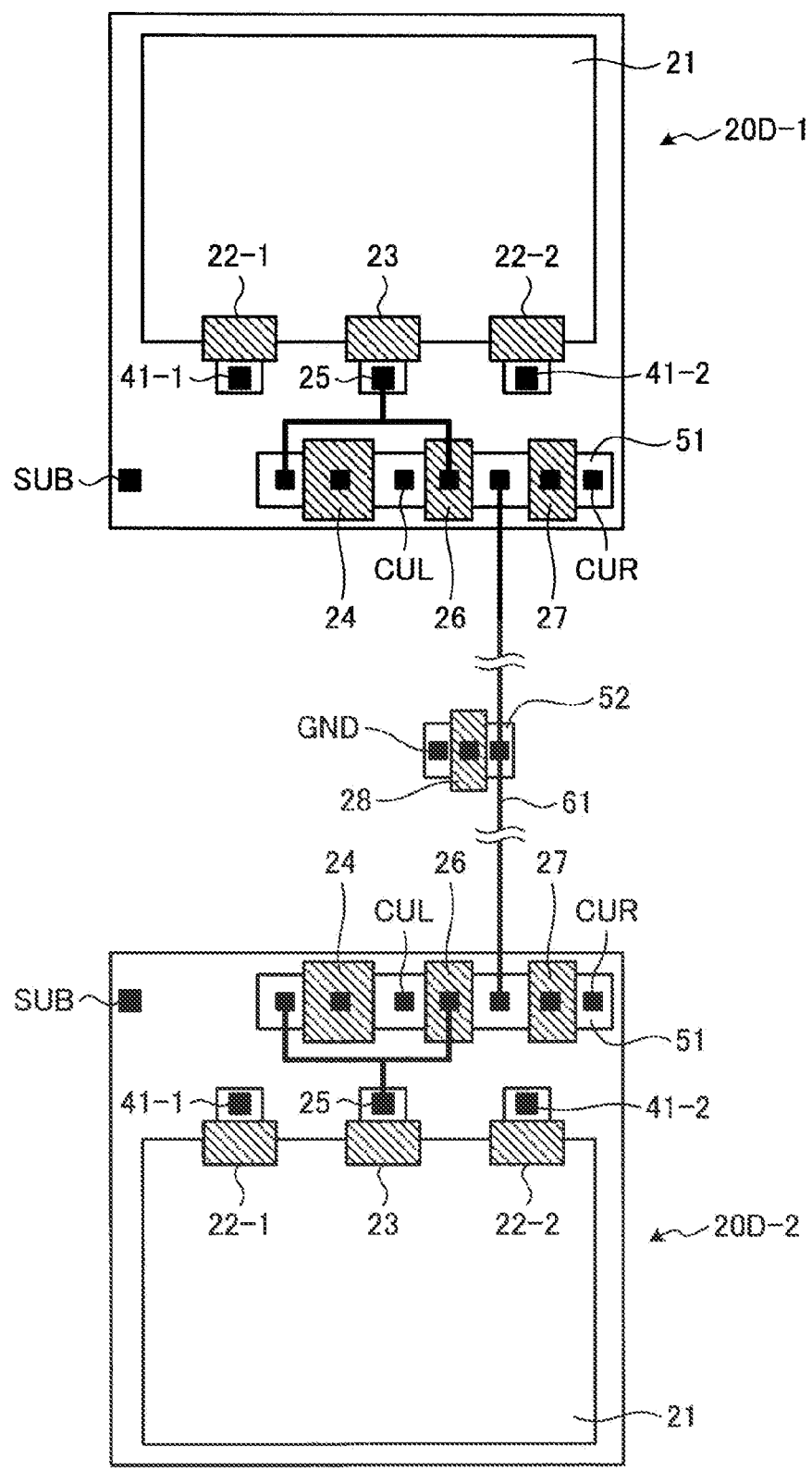
FIG. 11 is a schematic diagram depicting an example of an arrangement of the transistors in the pixel according to the fourth modification of the embodiment of the present disclosure.

FIG. 11 is a schematic diagram depicting an example of sharing the bias transistor 26 between pixel circuits provided on different substrates. As depicted in FIG. 11, the bias transistor 28 may be provided on a substrate between a substrate on which the first pixel circuit 20D-1 is arranged and a substrate on which the second pixel circuit 20D-2 is arranged. In addition, in FIG. 11, the bias transistor 28 may be arranged in, for example, the first pixel circuit 20D-1 or the second pixel circuit 20D-2. Further, in FIG. 11, the bias transistor 28 may be shared between the pixel circuits provided on a plurality of substrates with two or more layers.

Figure 12:
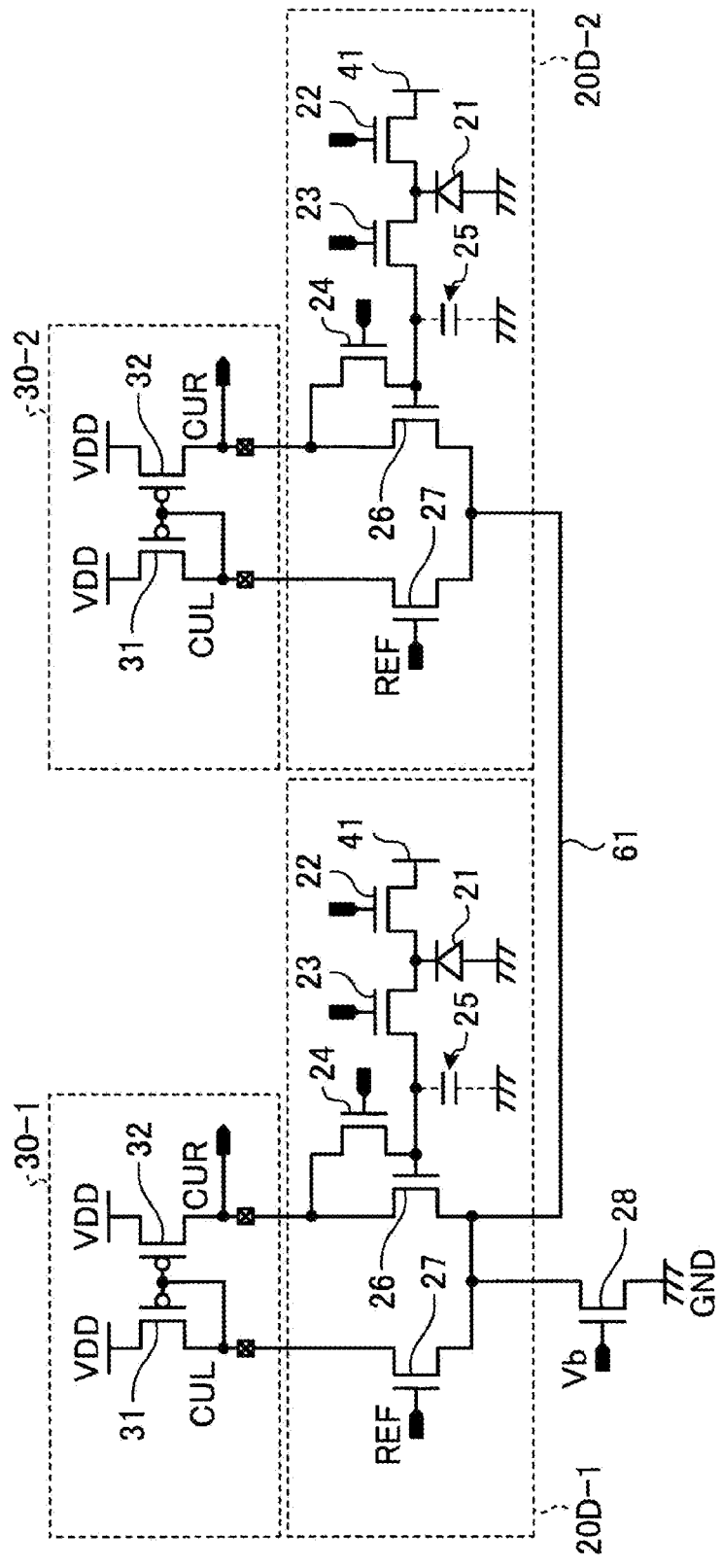
FIG. 12 is a circuit diagram depicting the pixel according to the fourth modification of the embodiment of the present disclosure.

FIG. 12 is a circuit diagram depicting a pixel circuit according to a fourth modification of the present embodiment. As depicted in FIG. 12, the first pixel circuit 20D-1 and the second pixel circuit 20D-2 each have a circuit configuration similar to that of the pixel circuit 20 depicted in FIG. 4, except that the bias transistor 28 is provided outside. In addition, in the fourth modification, the first pixel circuit 20D-1 is connected with a first current mirror circuit 30-1, and the second pixel circuit 20D-2 is connected with a second current mirror circuit 30-2.

It is to be noted that, in FIG. 10 to FIG. 12, the configuration in which one bias transistor provided outside the pixel circuit is shared between two pixel circuits has been described. However, this is an illustrative example and does not limit the present disclosure. In the present disclosure, one bias transistor provided outside may be shared among three or more pixel circuits. Further, two or more bias transistors provided outside may be shared among plural pixel circuits. Provision of two or more bias transistors enables a plurality of pixel circuits to stably receive the bias current.

6. Fifth Modification

Figure 13:
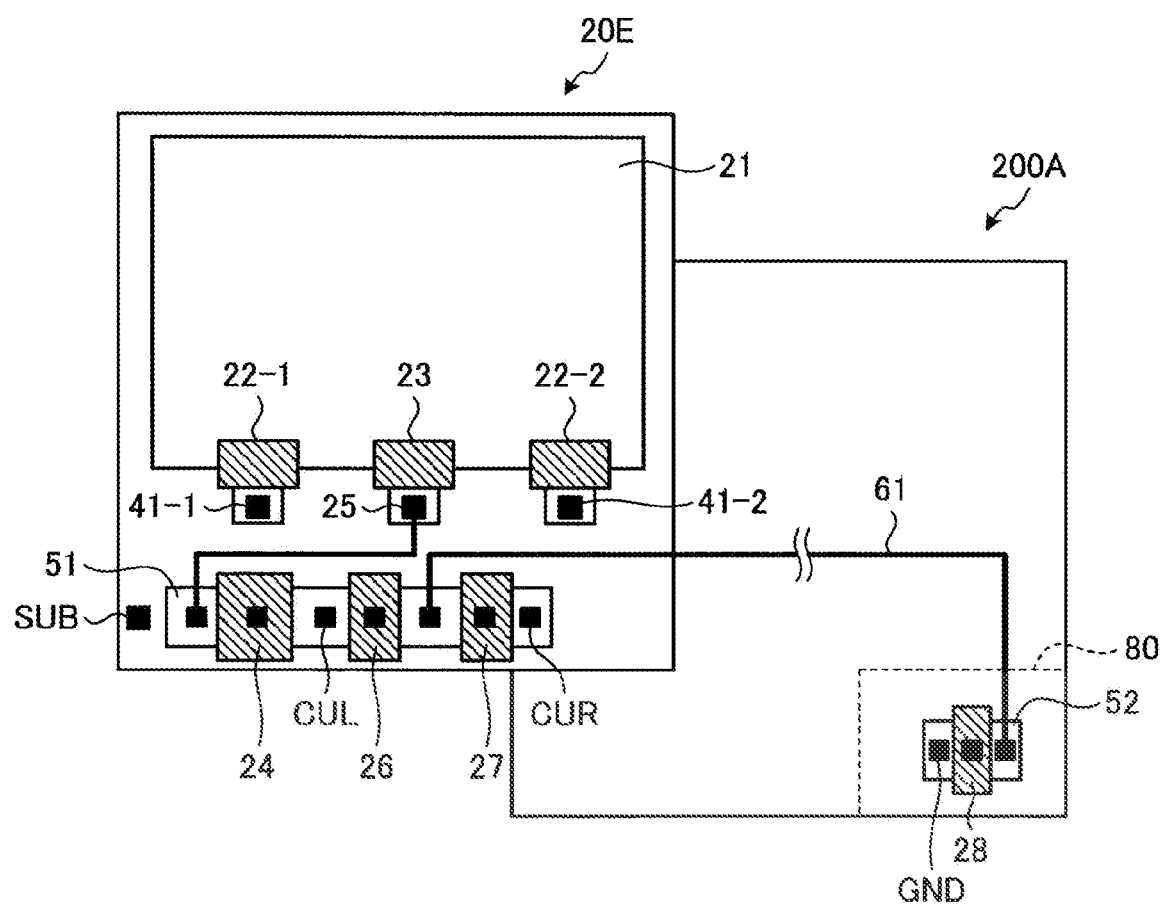
FIG. 13 is a schematic diagram depicting an example of an arrangement of transistors is a pixel according to a fifth modification of the embodiment of the present disclosure.

Referring to FIG. 13, an arrangement of transistors in a pixel according to a fifth modification of the present embodiment will be described. FIG. 13 is a schematic diagram depicting the arrangement of the transistors in the pixel according to the fifth modification of the present embodiment.

As depicted in FIG. 13, a pixel circuit 20E according to the present embodiment is different from the pixel circuit 20 depicted in FIG. 5 in that the bias transistor 28 is provided on a substrate different from the substrate on which the pixel circuit 20E is provided.

Figure 14:
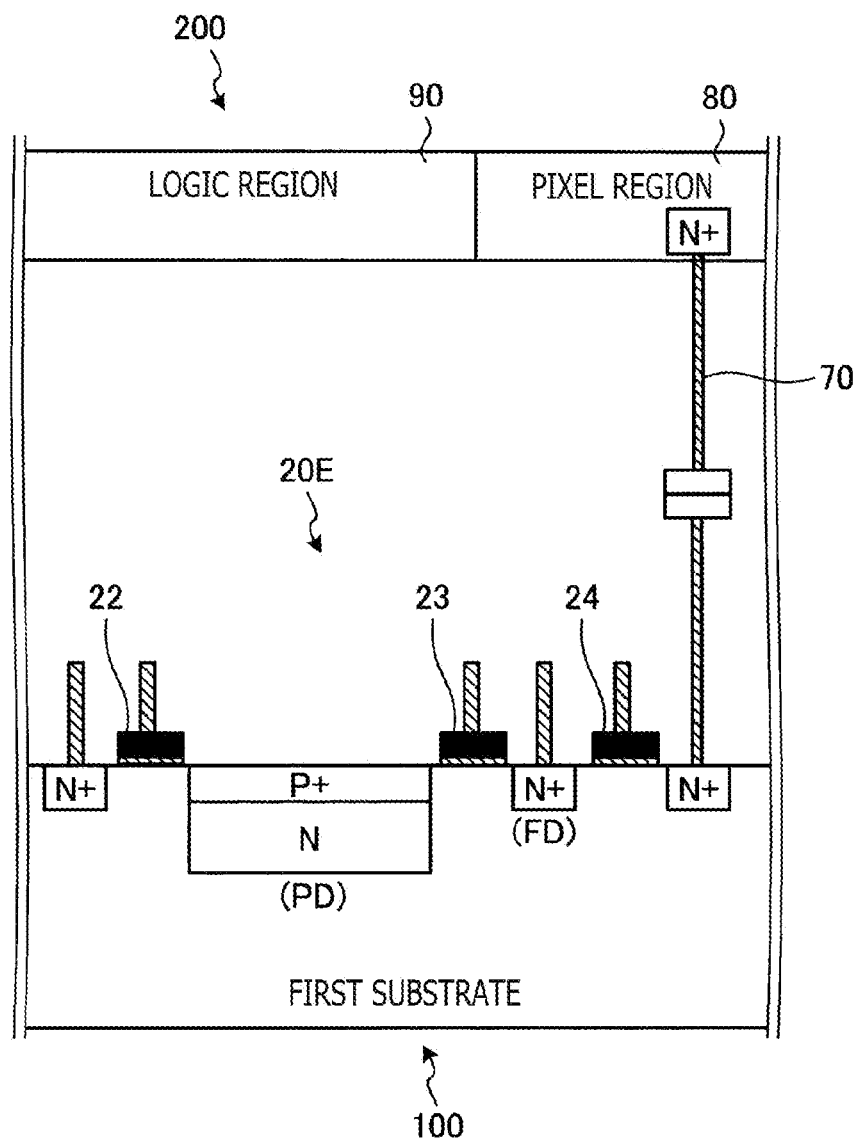
FIG. 14 is a schematic diagram depicting an example of a configuration in cross section of the pixel according to the fifth modification of the embodiment of the present disclosure.

FIG. 14 is a schematic diagram depicting an example in cross section of the pixel circuit 20E. In the example depicted in FIG. 14, for example, the pixel circuit 20E is arranged on the first substrate 100. Then, a second substrate 200A, which is laminated on the first substrate 100, includes, for example, a pixel region 80 and a logic region 90. In this case, for example, the bias transistor 28 is provided in the pixel region 80 of the second substrate 200A, which is different from the first substrate 100, and supplies the bias current to the amplification transistor 26 and the reference transistor 27, which are not depicted in FIG. 14. It is to be noted that the bias transistor 28, for example, may be arranged in the logic region 90. In FIG. 14, the configuration of the first substrate 100 is similar to that of FIG. 6, and the description is omitted.

7. Sixth Modification

Figure 15:
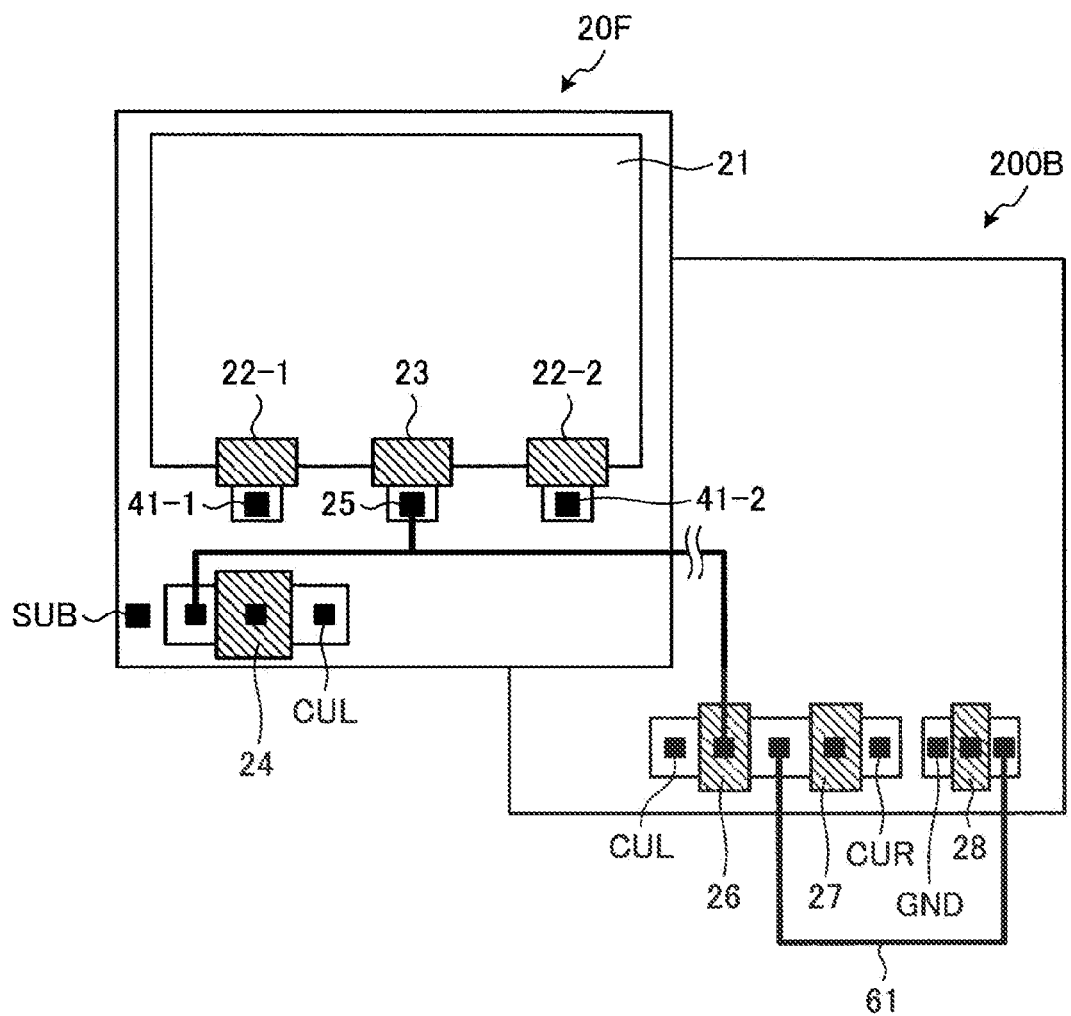
FIG. 15 is a schematic diagram depicting an example of an arrangement of transistors in a pixel according to a sixth modification of the embodiment of the present disclosure.

Referring to FIG. 15, an arrangement of transistors in a pixel according to a sixth modification of the present embodiment will be described. FIG. 15 is a schematic diagram depicting the arrangement of the transistors in the pixel according to the sixth modification of the present embodiment.

As depicted in FIG. 15, a pixel circuit 20F according to the present embodiment is different from the pixel circuit 20 depicted in FIG. 5 in that the amplification transistor 26, the reference transistor 27, and the bias transistor 28 are provided on a substrate different from the substrate on which the pixel circuit 20F is provided.

The cross section in the sixth modification has a configuration similar to that of the pixel circuit 20E in the fifth modification depicted in FIG. 14. In this case, the amplification transistor 26, the reference transistor 27, and the bias transistor 28 are arranged, for example, in the pixel region 80. It is to be noted that the amplification transistor 26, the reference transistor 27, and the bias transistor 28 may be arranged in the logic region 90. In addition, the amplification transistor 26, the reference transistor 27, and the bias transistor 28 may be separated and arranged in the pixel region 80 and the logic region 90.

Figure 16:
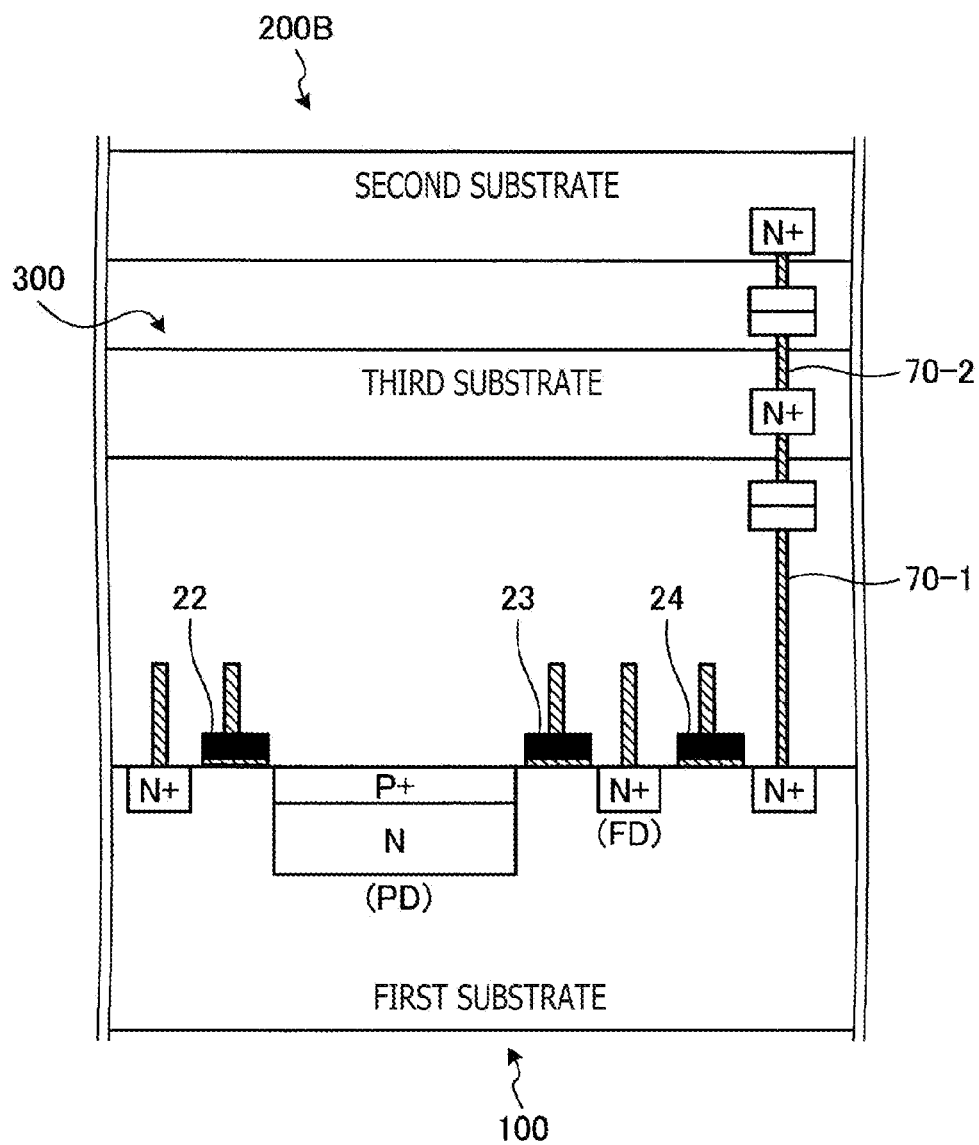
FIG. 16 is a schematic diagram depicting an example of a configuration in cross section of the pixel according to the sixth modification of the embodiment of the present disclosure.

Further, in the sixth modification, the amplification transistor 26, the reference transistor 27, and the bias transistor 28 may be separated and arranged on, for example, three or more substrates. FIG. 16 is a schematic diagram depicting an example in cross section of a pixel circuit 20F. In the example of FIG. 16, the first substrate 100, a second substrate 200B, and a third substrate 300 are depicted. Here, it is assumed that the pixel circuit 20F is arranged on, for example, the first substrate 100. In addition, it is assumed that the second substrate 200B is a logic substrate on which a peripheral circuit such as a logic circuit is arranged. Further, it is assumed that the third substrate 300 located between the first substrate 100 and the second substrate 200B is a pixel substrate.

In the case depicted in FIG. 16, the amplification transistor 26, the reference transistor 27, and the bias transistor 28 are separated and arranged on, for example, the second substrate 200B and the third substrate 300. In this case, for example, it is sufficient if the amplification transistor 26 and the reference transistor 27 are arranged on the second substrate 200B and the bias transistor 28 is arranged on the third substrate 300. In this case, the first substrate 100 and the third substrate 300 are connected with each other through connection wiring 70-1, which is provided so as to connect respective N+ layers formed on the first substrate 100 and the third substrate 300. In addition, the second substrate 200B and the third substrate 300 are connected with each other through connection wiring 70-2, which is provided so as to connect respective N+ layers formed on the second substrate 200B and the third substrate 300.

8. Application Example to Solid-State Imaging Device

Further, each solid-state imaging element as described above can be applied to various types of electronic equipment including, for example, an imaging system such as a digital still camera or a digital video camera, a mobile telephone equipped with an imaging function, or any other apparatus equipped with as imaging function.

Figure 17:
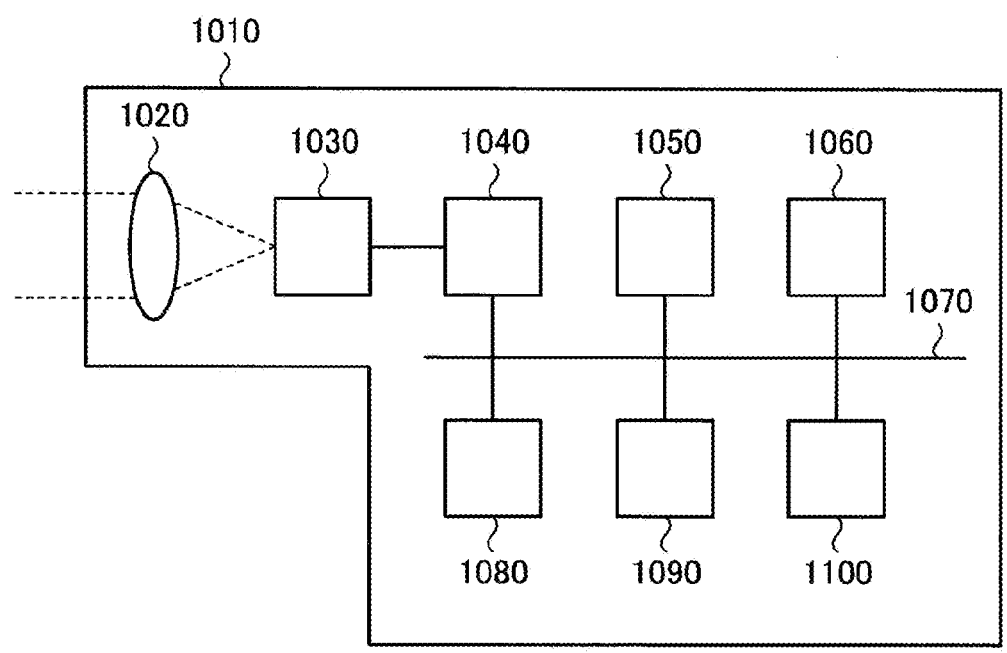
FIG. 17 is a block diagram depicting a configuration example of a solid-state imaging device.

Referring to FIG. 17, a configuration example of a solid-state imaging device mounted on electronic equipment will be described. FIG. 17 is a block diagram depicting the configuration example of the solid-state imaging device mounted on the electronic equipment.

As depicted in FIG. 17, a solid-state imaging device 1010 includes an optical system 1020, a solid-state imaging element 1030, and a DSP (Digital Signal Processor) 1040. The DSP 1040 is configured by connecting a display device 1050, an operation system 1060, a memory 1080, a recording device 1090, and a power supply system 1100 via a bus 1070. Since the solid-state imaging device 1010 has such a structure, the solid-state imaging device 1010 is capable of imaging a still image and a moving image.

The optical system 1020 includes one or a plurality of lenses, guides an imaging light (incident light) from a subject to the solid-state imaging element 1030, and forms an image on a light-receiving surface (sensor unit) of the solid-state imaging element 1030.

To the solid-state imaging element 1030, each solid-state imaging element described above is applied. In the solid-state imaging element 1030, electrons are accumulated for a certain period of time according to an image formed on the light-receiving surface via the optical system 1020. Then, a signal corresponding to the electrons accumulated in the solid-state imaging element 1030 is supplied to the DSP 1040.

The DSP 1040 performs various types of signal processing on signals from the solid-state imaging element 1030 to acquire an image, and temporarily stores the data of the image in the memory 1080. The data of the image stored in the memory 1080 is recorded in the recording device 1090, or is supplied to the display device 1050 to display an image. In addition, the operation system 1060 receives various kinds of operations from a user, and supplies an operation signal to each block of the solid-state imaging device 1010. The power supply system 1100 supplies the power necessary for driving each block of the solid-state imaging device 1010.

9. Application Example to Endoscopic Surgery System

The technology according to the present disclosure (present technology) can be applied to various products. For example, the technology according to the present disclosure may be applied to an endoscopic surgery system.

Figure 18:
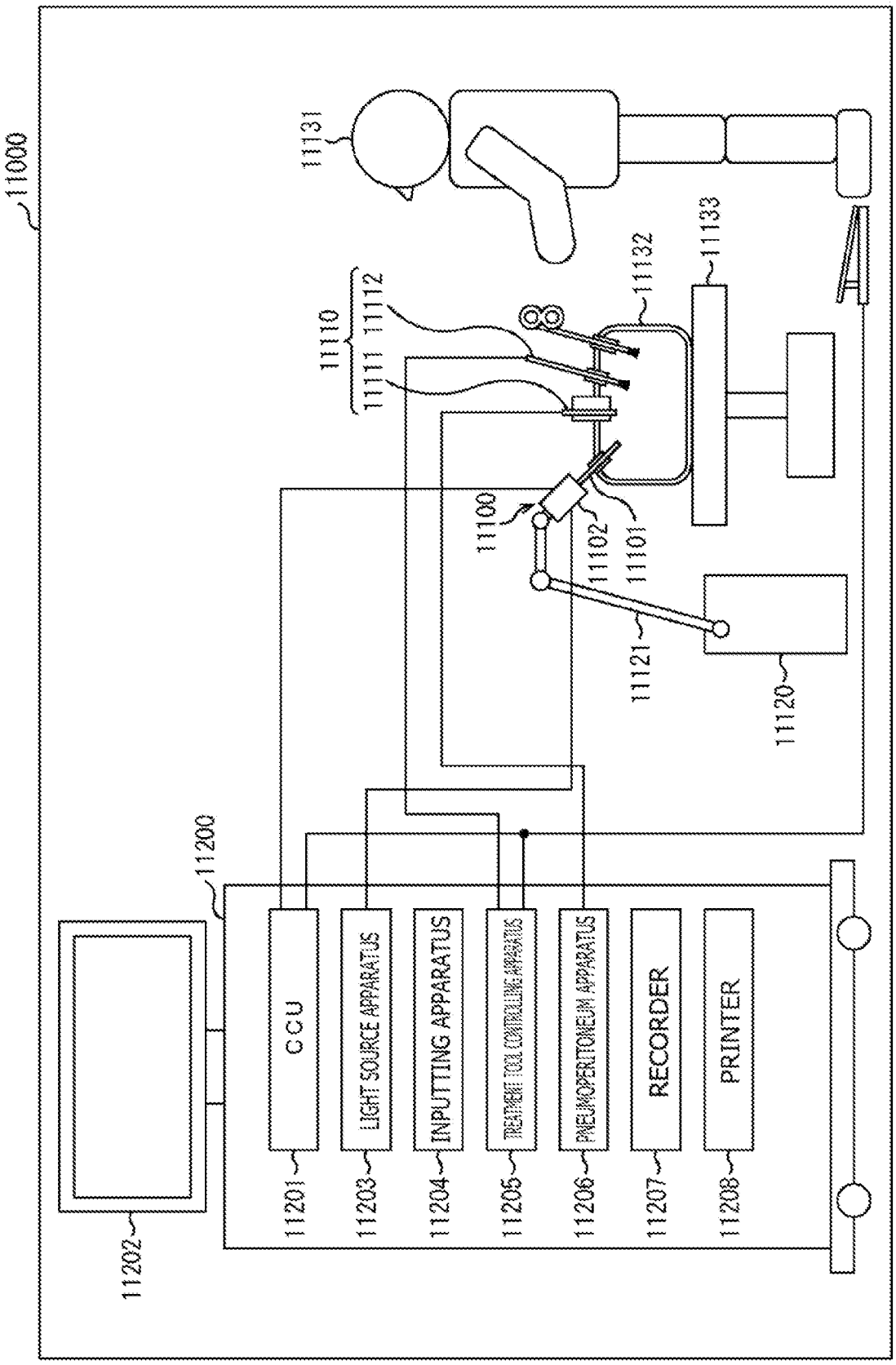
FIG. 18 is a view depicting an example of a schematic configuration of an endoscopic surgery system.

FIG. 18 is a view depicting an example of a schematic configuration of an endoscopic surgery system to which the technology according to an embodiment of the present disclosure (present technology) can be applied.

In FIG. 18, a state is illustrated in which a surgeon (medical doctor) 11131 is using an endoscopic surgery system 11000 to perform surgery for a patient 11132 on a patient bed 11133. As depicted, the endoscopic surgery system 11000 includes an endoscope 11100, other surgical tools 11110 such as a pneumoperitoneum tube 11111 and an energy device 11112, a supporting arm apparatus 11120 which supports the endoscope 11100 thereon, and a cart 11200 on which various apparatus for endoscopic surgery are mounted.

The endoscope 11100 includes a lens barrel 11101 having a region of a predetermined length from a distal end thereof to be inserted into a body cavity of the patient 11132, and a camera head 11102 connected to a proximal end of the lens barrel 11101. In the example depicted, the endoscope 11100 is depicted which includes as a rigid endoscope having the lens barrel 11101 of the hard type. However, the endoscope 11100 may otherwise be included as a flexible endoscope having the lens barrel 11101 of the flexible type.

The lens barrel 11101 has, at a distal end thereof, an opening in which an objective lens is fitted. A light source apparatus 11203 is connected to the endoscope 11100 such that light generated by the light source apparatus 11203 is introduced to a distal end of the lens barrel 11101 by a light guide extending in the inside of the lens barrel 11101 and is irradiated toward an observation target in a body cavity of the patient 11132 through the objective lens. It is to be noted that the endoscope 11100 may be a forward-viewing endoscope or may be an oblique-viewing endoscope or a side-viewing endoscope.

An optical system and an image pickup element are provided in the inside of the camera head 11102 such that reflected light (observation light) from the observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a camera control unit (CCU) 11201.

The CCU 11201 includes a central processing unit (CPU), a graphics processing unit (GPU) or the like and integrally controls operation of the endoscope 11100 and a display apparatus 11202. Further, the CCU 11201 receives an image signal from the camera head 11102 and performs, for the image signal, various image processes for displaying an image based on the image signal such as, for example, a development process (demosaic process).

The display apparatus 11202 displays thereon an image based on an image signal, for which the image processes have been performed by the CCU 11201, under the control of the CCU 11201.

The light source apparatus 11203 includes a light source such as, for example, a light emitting diode (LED) and supplies irradiation light upon imaging of a surgical region to the endoscope 11100.

An inputting apparatus 11204 is an input interface for the endoscopic surgery system 11000. A user can perform inputting of various kinds of information or instruction inputting to the endoscopic surgery system 11000 through the inputting apparatus 11204. For example, the user would input an instruction or a like to change an image pickup condition (type of irradiation light, magnification, focal distance or the like) by the endoscope 11100.

A treatment tool controlling apparatus 11205 controls driving of the energy, device 11112 for cautery or incision of a tissue, sealing of a blood vessel or the like. A pneumoperitoneum apparatus 11206 feeds gas into a body cavity of the patient 11132 through the pneumoperitoneum tube 11111 to inflate the body cavity in order to secure the field of view of the endoscope 11100 and secure the working space for the surgeon. A recorder 11207 is an apparatus capable of recording various kinds of information relating to surgery. A printer 11208 is an apparatus capable of printing various kinds of information relating to surgery in various forms such as a text, an image or a graph.

It is to be noted that the light source apparatus 11203 which supplies irradiation light when a surgical region is to be imaged to the endoscope 11100 may include a white light source which includes, for example, an LED, a laser light source or a combination of them. Where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 11203. Further, in this case, if laser beams from the respective RGB laser light sources are irradiated time-divisionally on an observation target and driving of the image pickup elements of the camera head 11102 are controlled in synchronism with the irradiation timings. Then images individually corresponding to the R, G and B colors can be also picked up time-divisionally. According to this method, a color image can be obtained even if color filters are not provided for the image pickup element.

Further, the light source apparatus 11203 may be controlled such that the intensity of light to be outputted is changed for each predetermined time. By controlling driving of the image pickup element of the camera head 11102 in synchronism with the timing of the change of the intensity of light to acquire images time-divisionally and synthesizing the images, an image of a high dynamic range free from underexposed blocked up shadows and overexposed highlights can be created.

Further, the light source apparatus 11203 may be configured to supply light of a predetermined wavelength band ready for special light observation. In special light observation, for example, by utilizing the wavelength dependency of absorption of light in a body tissue to irradiate light of a narrow band in comparison with irradiation light upon ordinary observation (namely, white light), narrow band observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 11203 can be configured to supply such narrow-hand light and/or excitation light suitable for special light observation as described above.

Figure 19:
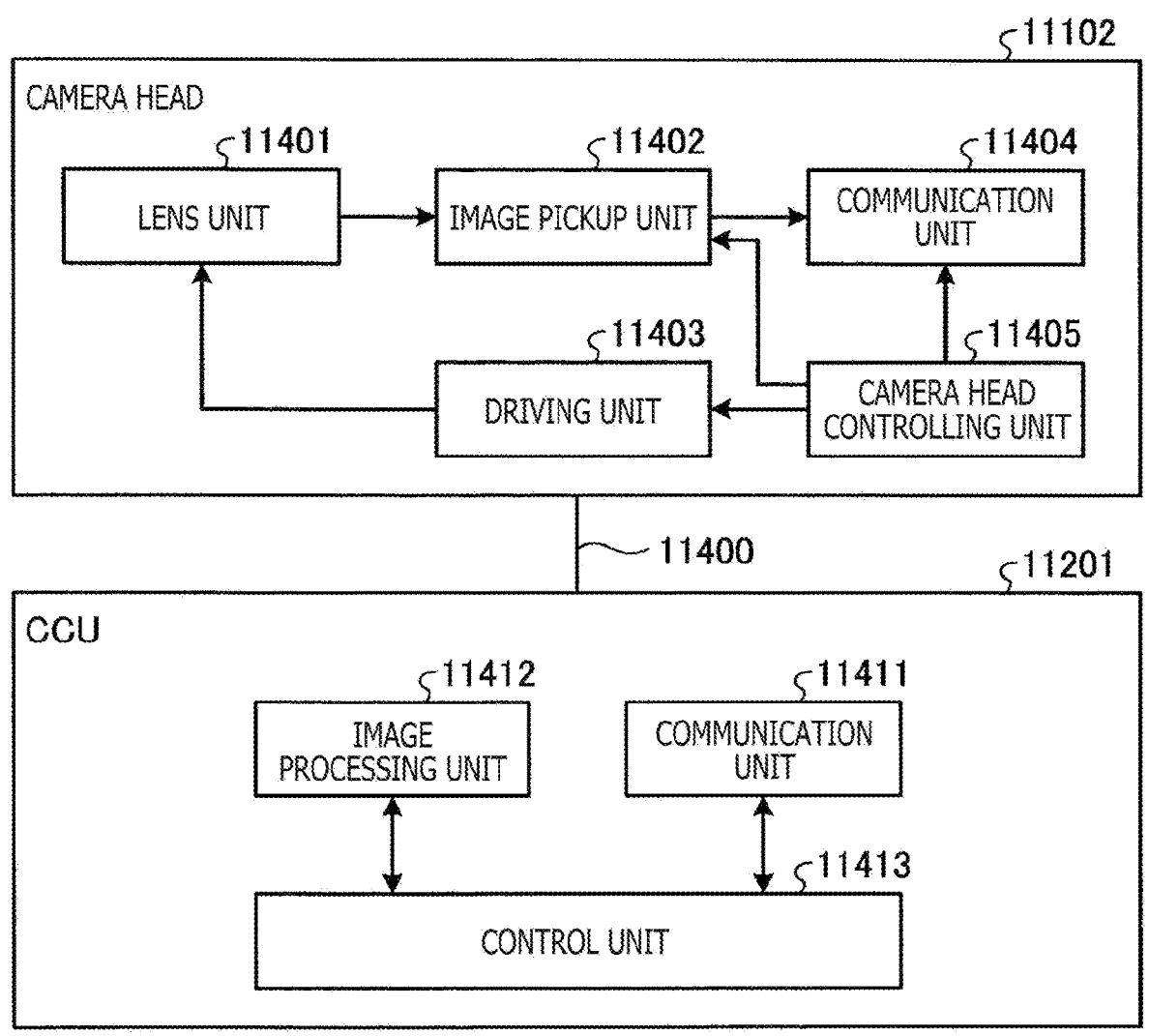
FIG. 19 is a block diagram depicting an example of a functional configuration of a camera head and a CCU.

FIG. 19 is a block diagram depicting an example of a functional configuration of the camera head 11102 and the CCU 11201 depicted in FIG. 18.

The camera head 11102 includes a lens unit 11401, an image pickup unit 11402, a driving unit 11403, a communication unit 11404 and a camera head controlling unit 11405. The CCU 11201 includes a communication unit 11411, as image processing unit 11412 and a control unit 11413. The camera head 11102 and the CCU 11201 are connected for communication to each other by a transmission cable 11400.

The lens unit 11401 is an optical system, provided at a connecting location to the lens barrel 11101. Observation light taken is from a distal end of the lens barrel 11101 is guided to the camera head 11102 and introduced into the lens unit 11401. The lens unit 11401 includes a combination of a plurality of lenses including a zoom lens and a focusing lens.

The image pickup unit 11402 includes image pickup elements. The number of image pickup elements which is included by the image pickup unit 11402 may be one (single-plate type) or a plural number (multi-plate type). Where the image pickup unit 11402 is configured as that of the multi-plate type, for example, image signals corresponding to respective R, G and B are generated by the image pickup elements, and the image signals may be synthesized to obtain a color image. The image pickup unit 11402 may also be configured so as to have a pair of image pickup elements for acquiring respective image signals for the right eye and the left eye ready for three dimensional (3D) display. If 3D display is performed, then the depth of a living body tissue in a surgical region can be comprehended more accurately by the surgeon 11131. It is to be noted that, where the image pickup unit 11402 is configured as that of stereoscopic type, a plurality of systems of lens units 11401 are provided corresponding to the individual image pickup elements.

Further, the image pickup unit 11402 may not necessarily be provided on the camera head 11102. For example, the image pickup unit 11402 may be provided immediately behind the objective lens in the inside of the lens barrel 11101.

The driving unit 11403 includes an actuator and moves the zoom lens and the focusing lens of the lens unit 11401 by a predetermined distance along an optical axis under the control of the camera head controlling unit 11405. Consequently, the magnification and the focal point of a picked up image by the image pickup unit 11402 can be adjusted suitably.

The communication unit 11404 includes a communication apparatus for transmitting and receiving various kinds of information to and from the CCU 11201. The communication unit 11404 transmits an image signal acquired from the image pickup unit 11402 as RAW data to the CCU 11201 through the transmission cable 11400.

In addition, the communication unit 11404 receives a control signal for controlling driving of the camera head 11102 from the CCU 11201 and supplies the control signal to the camera head controlling unit 11405. The control signal includes information relating to image pickup conditions such as, for example, information that a frame rate of a picked up image is designated, information that an exposure value upon image picking up is designated and/or information that a magnification and a focal point of a picked up image are designated.

It is to be noted that the image pickup conditions such as the frame rate, exposure value, magnification or focal point may be designated by the user or may be set automatically by The control unit 11413 of the CCU 11201 on the basis of an acquired image signal. In the latter case, an auto exposure (AE) function, an auto focus (AF) function and an auto white balance (AWB) function are incorporated in the endoscope 11100.

The camera head controlling unit 11405 controls driving of the camera head 11102 on the basis of a control signal from the CCU 11201 received through the communication unit 11404.

The communication unit 11411 includes a communication apparatus for transmitting and receiving various kinds of information to and from the camera head 11102. The communication unit 11411 receives an image signal transmitted thereto from the camera head 11102 through the transmission cable 11400.

Further, the communication unit 11411 transmits a control signal for controlling driving of the camera head 11102 to the camera head 11102. The image signal and the control signal can be transmitted by electrical communication, optical communication or the like.

The image processing unit 11412 performs various image processes for an image signal in the form of RAW data transmitted thereto from the camera head 11102.

The control unit 11413 performs various kinds of control relating to image picking up of a surgical region or the like by the endoscope 11100 and display of a picked up image obtained by image picking up of the surgical region or the like. For example, the control unit 11413 creates a control signal for controlling driving of the camera head 11102.

Further, the control unit 11413 controls, on the basis of an image signal for which image processes have been performed by the image processing unit 11412, the display apparatus 11202 to display a picked up image in which the surgical region or the like is imaged. Thereupon, the control unit 11413 may recognize various objects in the picked up image using various image recognition technologies. For example, the control unit 11413 can recognize a surgical tool such as forceps, a particular living body region, bleeding, mist when the energy device 11112 is used and so forth by detecting the shape, color and so forth of edges of objects included in a picked up image. The control unit 11413 may cause, when it controls the display apparatus 11202 to display a picked up image, various kinds of surgery supporting information to be displayed in an overlapping manner with an image of the surgical region using a result of the recognition. Where surgery supporting information is displayed in an overlapping manner and presented to the surgeon 11131, the burden on the surgeon 11131 can be reduced and the surgeon 11131 can proceed with the surgery with certainty.

The transmission cable 11400 which connects the camera head 11102 and the CPU 11201 to each other is an electric signal cable ready for communication of an electric signal, an optical fiber ready for optical communication or a composite cable ready for both of electrical and optical communications.

Here, while, in the example depicted, communication is performed by wired communication using the transmission cable 11400, the communication between the camera head 11102 and the CCU 11201 may be performed by wireless communication.

Heretofore, an example of the endoscopic surgery system to which the technology according to the present disclosure can be applied has been described. The technology according to the present disclosure can be applied to, for example, the image pickup unit 11402, in the configuration described above. For example, the solid-state imaging element 1 of FIG. 1 can be applied to the image pickup unit 11402.

It is to be noted that here, the endoscopic surgery system has been described as an example. However, the technology according to the present disclosure may be applied to another system, for example, a surgical microscope system or the like.

10. Application Example to Mobile Body

The technology according to the present disclosure (present technology) can be applied to various products. For example, the technology according to the present disclosure may be realized as a device to be mounted on any kind of a mobile body, such as automobile, electric vehicle, hybrid electric vehicle, motorcycle, bicycle, personal mobility, airplane, drone, marine vessel, and robot.

Figure 20:
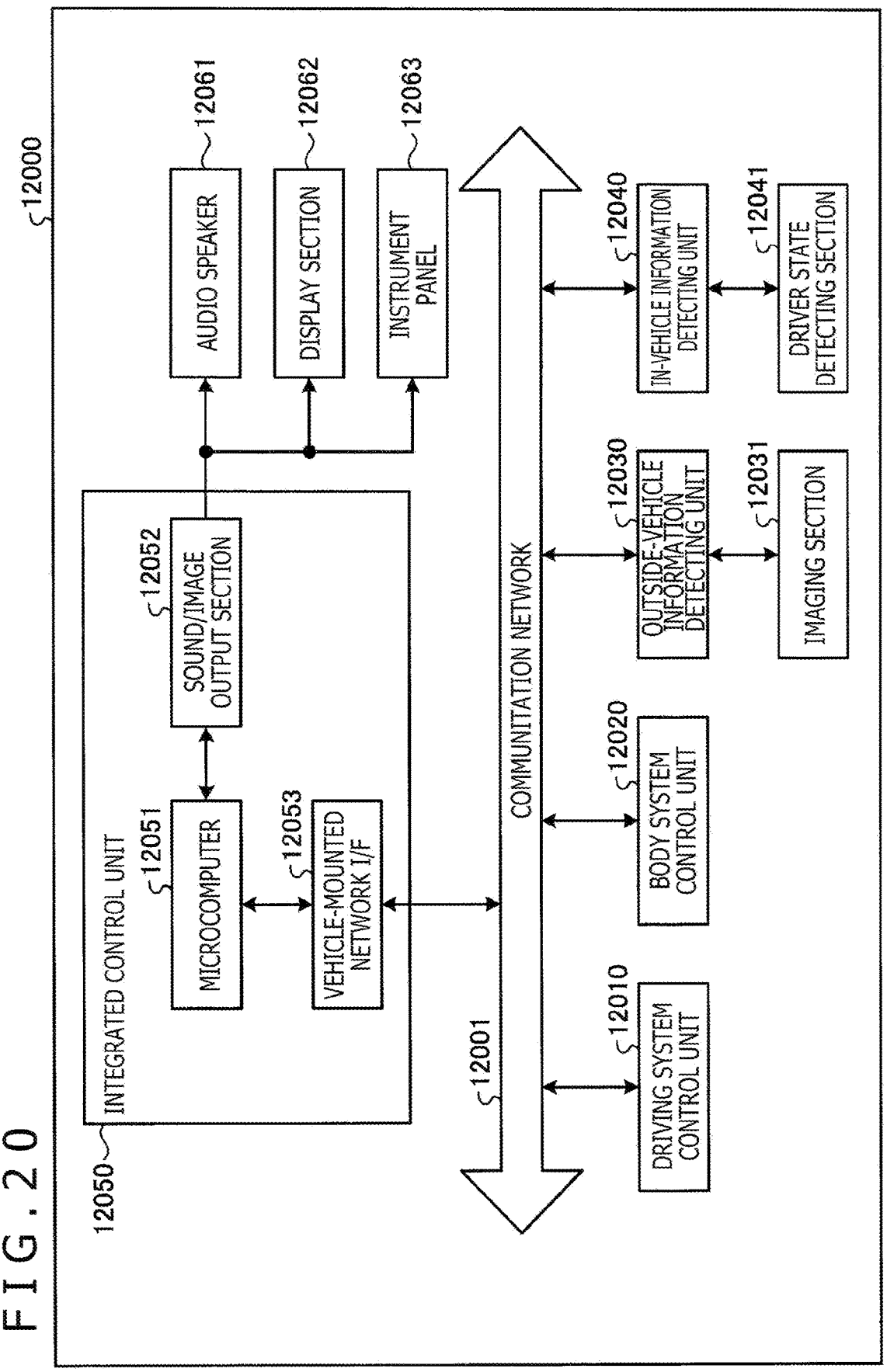
FIG. 20 is a block diagram depicting an example of a schematic configuration of a vehicle control system.

FIG. 20 is a block diagram depicting an example of schematic configuration of a vehicle control system as an example of a mobile body control system to which the technology according to an embodiment of the present disclosure can be applied.

The vehicle control system 12000 includes a plurality of electronic control units connected to each other via a communication network 12001. In the example depicted in FIG. 20, the vehicle control system 12000 includes a driving system control unit 12010, a body system control unit 12020, an outside-vehicle information detecting unit 12030, an in-vehicle information detecting unit 12040, and an integrated control unit 12050. In addition, a microcomputer 12051, a sound/image output section 12052, and a vehicle-mounted network interface (I/F) 12053 are illustrated as a functional configuration of the integrated control unit 12050.

The driving system control unit 12010 controls the operation of devices related to the driving system of the vehicle in accordance with various kinds of programs. For example, the driving system control unit 12010 functions as a control device for a driving force generating device for generating the driving force of the vehicle, such as an internal combustion engine, a driving motor, or the like, a driving force transmitting mechanism for transmitting the driving force to wheels, a steering mechanism for adjusting the steering angle of the vehicle, a braking device for generating the braking force of the vehicle, and the like.

The body system control unit 12020 controls the operation of various kinds of devices provided to a vehicle body in accordance with various kinds of programs. For example, the body system control unit 12020 functions as a control device for a keyless entry system, a smart key system, a power window device, or various kinds of lamps such as a headlamp, a backup lamp, a brake lamp, a turn signal, a fog lamp, or the like. In this case, radio waves transmitted from a mobile device as an alternative to a key or signals of various kinds of switches can be input to the body system control unit 12020. The body system control unit 12020 receives these input radio waves or signals, and controls a door lock device, the power window device, the lamps, or the like of the vehicle.

The outside-vehicle information detecting unit 12030 detects information about the outside of the vehicle including the vehicle control system 12000. For example, the outside-vehicle information detecting unit 12030 is connected with an imaging section 12031. The out side-vehicle information detecting unit 12030 makes the imaging section 12031 image an image of the outside of the vehicle, and receives the imaged image. On the basis of the received image, the outside-vehicle information detecting unit 12030 may perform processing of detecting an object such as a human, a vehicle, an obstacle, a sign, a character on a road surface, or the like, or processing of detecting a distance thereto.

The imaging section 12031 is an optical sensor that receives light, and which outputs an electric signal corresponding to a received light amount of the light. The imaging section 12031 can output the electric signal as an image, or can output the electric signal as information about a measured distance. In addition, the light received by the imaging section 12031 may be visible light, or may be invisible light such as infrared rays or the like.

The in-vehicle information detecting unit 12040 detects information about the inside of the vehicle. The in-vehicle information detecting unit 12040 is, for example, connected with a driver state detecting section 12041 that detects the state of a driver. The driver state detecting section 12041, for example, includes a camera that images the driver. On the basis of detection information input from the driver state detecting section 12041, the in-vehicle information detecting unit 12040 may calculate a degree of fatigue of the driver or a degree of concentration of the driver, or may determine whether the driver is dozing.

The microcomputer 12051 can calculate a control target value for the driving force generating device, the steering mechanism, or the braking device on the basis of the information about the inside or outside of the vehicle which information is obtained by the outside-vehicle information detecting unit 12030 or the in-vehicle information detecting unit 12040, and output a control command to the driving system control unit 12010. For example, the microcomputer 12051 can perform cooperative control intended to implement functions of an advanced driver assistance system (ADAS) which functions include collision avoidance or shock mitigation for the vehicle, following driving based on a following distance, vehicle speed maintaining driving, a warning of collision of the vehicle, a warning of deviation of the vehicle from a lane, or the like.

In addition, the microcomputer 12051 can perform cooperative control intended for automatic driving, which makes the vehicle to travel autonomously without depending on the operation of the driver, or the like, by controlling the driving force generating device, the steering mechanism, the braking device, or the like on the basis of the information about the outside or inside of the vehicle which information is obtained by the outside-vehicle information detecting unit 12030 or the in-vehicle information detecting unit 12040.

In addition, the microcomputer 12051 can output a control command to the body system control unit 12020 on the basis of the information about the outside of the vehicle which information is obtained by the outside-vehicle information detecting unit 12030. For example, the microcomputer 12051 can perform cooperative control intended to prevent a glare by controlling the headlamp so as to change from a high beam to a low beam, for example, in accordance with the position of a preceding vehicle or an oncoming vehicle detected by the outside-vehicle information detecting unit 12030.

The sound/image output section 12052 transmits an output signal of at least one of a sound and an image to an output device capable of visually or auditorily notifying information to an occupant of the vehicle or the outside of the vehicle. In the example of FIG. 20, an audio speaker 12061, a display section 12062, and an instrument panel 12063 are illustrated as the output device. The display section 12062 may, for example, include at least one of an on-board display and a head-up display.

Figure 21:
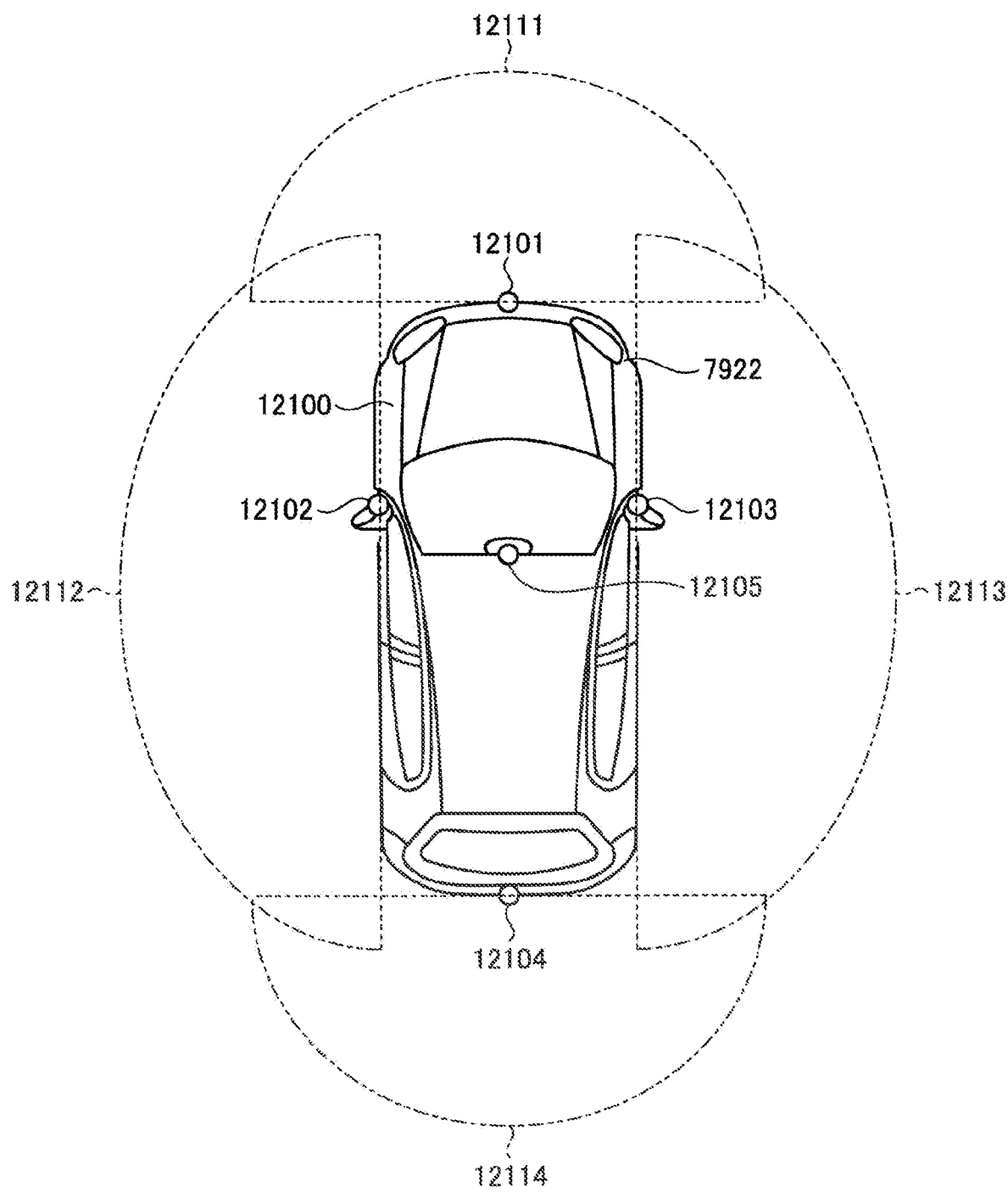
FIG. 21 is a diagram for describing an example of installation positions of an outside-vehicle information detecting section and an imaging section.

FIG. 21 is a diagram depicting an example of the installation position of the imaging section 12031.

In FIG. 21, the vehicle 12100 includes, as the imaging section 12031, imaging sections 12101, 12102, 12103, 12104, and 12105.

The imaging sections 12101, 12102, 12103, 12104, and 12105 are, for example, disposed at positions on a front nose, sideview mirrors, a rear bumper, and a back door of the vehicle 12100 as well as a position on an upper portion of a windshield than the interior of the vehicle. The imaging section 12101 provided to the front nose and the imaging section 12105 provided to the upper portion of the windshield within the interior of the vehicle obtain mainly an image of the front of the vehicle 12100. The imaging sections 12102 and 12103 provided to the sideview mirrors obtain mainly an image of the sides of the vehicle 12100. The imaging section 12104 provided to the rear bumper or the back door obtains mainly an image of the rear of the vehicle 12100. The image of the front obtained by the imaging sections 12101 and 12105 is used mainly to detect a preceding vehicle, a pedestrian, an obstacle, a signal, a traffic sign, a lane, or the like.

Incidentally, FIG. 21 depicts an example of photographing ranges of the imaging sections 12101 to 12104. An imaging range 12111 represents the imaging range of the imaging section 12101 provided to the front nose. Imaging ranges 12112 and 12113 respectively represent the imaging ranges of the imaging sections 12102 and 12103 provided to the sideview mirrors. An imaging range 12114 represents the imaging range of the imaging section 12104 provided to the rear bumper or the back door. A bird's-eye image of the vehicle 12100 as viewed from above is obtained by superimposing image data imaged by the imaging sections 12101 to 12104, for example.

At least one of the imaging sections 12101 to 12104 may have a function of obtaining distance information. For example, at least one of the imaging sections 12101 to 12104 may be a stereo camera constituted of a plurality of imaging elements, or may be an imaging element having pixels for phase difference detection.

For example, the microcomputer 12051 can determine a distance to each three-dimensional object within the imaging ranges 12111 to 12114 and a temporal change in the distance (relative speed with respect to the vehicle 12100) on the basis of the distance information obtained from the imaging sections 12101 to 12104, and thereby extract, as a preceding vehicle, a nearest three-dimensional object in particular that is present on a traveling path of the vehicle 12100 and which travels in substantially the same direction as the vehicle 12100 at a predetermined speed (for example, equal to or more than 0 km/h). Further, the microcomputer 12051 can set a following distance to be maintained in front of a preceding vehicle in advance, and perform automatic brake control (including following stop control), automatic acceleration control (including following start control), or the like. It is thus possible to perform cooperative control intended for automatic driving that makes the vehicle travel autonomously without depending on the operation of the driver or the like.

For example, the microcomputer 12051 can classify three-dimensional object data on three-dimensional objects into three-dimensional object data of a two-wheeled vehicle, a standard-sized vehicle, a large-sized vehicle, a pedestrian, a utility pole, and other three-dimensional objects on the basis of the distance information obtained from the imaging sections 12101 to 12104, extract the classified three-dimensional object data, and use the extracted three-dimensional object data for automatic avoidance of an obstacle. For example, the microcomputer 12051 identifies obstacles around the vehicle 12100 as obstacles that the driver of the vehicle 12100 can recognize visually and obstacles that are difficult for the driver of the vehicle 12100 to recognize visually. Then, the microcomputer 12051 determines a collision risk indicating a risk of collision with each obstacle. In a situation in which the collision risk is equal to or higher than a set value and there is thus a possibility of collision, the microcomputer 12051 outputs a warning to the driver via the audio speaker 12061 or the display section 12062, and performs forced deceleration or avoidance steering via the driving system control unit 12010. The microcomputer 12051 can thereby assist in driving to avoid collision.

At least one of the imaging sections 12101 to 12104 may be an infrared camera that detects infrared rays. The microcomputer 12051 can, for example, recognize a pedestrian by determining whether or not there is a pedestrian in imaged images of the imaging sections 12101 to 12104. Such recognition of a pedestrian is, for example, performed by a procedure of extracting characteristic points in the imaged images of the imaging sections 12101 to 12104 as infrared cameras and a procedure of determining whether or not it is the pedestrian by performing pattern matching processing on a series of characteristic points representing the contour of the object. When the microcomputer 12051 determines that there is a pedestrian in the imaged images of the imaging sections 12101 to 12104, and thus recognizes the pedestrian, the sound/image output section 12052 controls the display section 12062 so that a square contour line for emphasis is displayed so as to be superimposed on the recognized pedestrian. The sound/image output section 12052 may also control the display section 12062 so that an icon or the like representing the pedestrian is displayed at a desired position.

Heretofore, an example of the vehicle control system to which the technology according to the present disclosure can be applied has been described. The technology according to the present disclosure can be applied to, for example, the imaging section 12031 in the configuration described above. Specifically, the solid-state imaging element 1 depicted in FIG. 1 can be applied to the imaging section 12031.

It is to be noted that the advantages described in the present description are merely illustrative examples and are not necessarily limited. Another advantage may be conceivable.

It is to be noted that the present technology can also take following configurations.

(1)

A solid-state imaging element including:

a pixel circuit in which a first transistor that amplifies a pixel signal is arranged, the pixel signal being generated by a photoelectric converter performing photoelectric conversion on light that has entered a pixel, the pixel circuit including a second transistor into which a reference signal is input from a reference signal generator, and a third transistor that outputs bias current to the first transistor and the second transistor.

(2)

The solid-state imaging element according to (1) above, in which sources of the first transistor and the second transistor are connected with a drain of the third transistor, the reference signal generator is connected with a gate of the second transistor, and a source of the third transistor is connected to a ground.

(3)

The solid-state imaging element according to (1) or (2) above, is which drains of the first transistor and the second transistor are connected with a current mirror circuit provided outside.

(4)

The solid-state imaging element according to any of (1) to (3) above, in which the first transistor, the second transistor, and the third transistor are linearly arranged in this order.

(5)

The solid-state imaging element according to (4) above, in which a source of the second transistor and a ground node with which a drain of the third transistor is connected are adjacent to each other.

(6)

The solid-state imaging element according to any of (1) to (5) above, in which the first transistor, the second transistor, and the third transistor share a diffusion layer.

(7)

The solid-state imaging element according to any of (1) to (6) above, in which the third transistor is shared by a plurality of the pixel circuits.

(8)

The solid-state imaging element according to (7) above, in which the third transistor is shared through routing wiring formed for connecting the plurality of the pixel circuits.

(9)

The solid-state imaging element according to (7) or (8) above, in which the plurality of the pixel circuits is provided on a plurality of semiconductor substrates that is laminated on top of another, and the third transistor is shared by the plurality of the pixel circuits provided on the plurality of semiconductor substrates.

(10)

The solid-state imaging element according to (1) above, including:

a first semiconductor substrate on which the pixel circuit is arranged; and a second semiconductor substrate which is laminated on the first semiconductor substrate and on which no pixel circuit is arranged, in which of the first transistor, the second transistor, and the third transistor, at least the third transistor is arranged is the pixel of the second semiconductor substrate.

(11)

The solid-state imaging element according to (10) above, in which the first transistor and the second transistor are arranged in the pixel of the second semiconductor substrate.

(12)

The solid-state imaging element according to (1) above, is which the first transistor, the second transistor, and the third transistor are arranged on a substrate different from a substrate on which the pixel circuit is arranged.

(13)

A solid-state imaging device including:

a solid-state imaging element; and an optical system configured to guide an incident light from a subject to the solid-state imaging element, the solid-state imaging element including a pixel circuit in which a first transistor that amplifies a pixel signal is arranged, the pixel signal being generated by a photoelectric converter performing photoelectric conversion on light that has entered a pixel, the pixel circuit including a second transistor into which a reference signal is input from a reference signal generator, and a third transistor that outputs bias current to the first transistor and the second transistor.

(14)

Electronic equipment on which a solid-state imaging device is mounted, the solid-state imaging device including:

a solid-state imaging element; and an optical system configured to guide an incident light from a subject to the solid-state imaging element, the solid-state imaging element including a pixel circuit in which a first transistor that amplifies a pixel signal is arranged, the pixel signal being generated by a photoelectric converter performing photoelectric conversion on light that has entered a pixel, the pixel circuit including
a second transistor into which a reference signal is input from a reference signal generator, and
a third transistor that outputs bias current to the first transistor and the second transistor.

REFERENCE SIGNS LIST

1: Solid-state imaging element
20: Pixel circuit
21: Photoelectric converter
22: Discharge transistor
23: Transfer transistor
24: Reset transistor
25: Floating diffusion layer (FD)
26: Amplification transistor (first transistor)
27: Reference transistor (second transistor)
28: Bias transistor (third transistor)
30: Current mirror circuit
31, 32: Transistors
100: First substrate
110: Pixel array unit
111: Pixel
200: Second substrate
210: Logic circuit
220: Pixel drive circuit
230: DAC
240: Vertical drive circuit
250: Timing generation circuit
260: Output unit
270: Peripheral circuit
300: Third substrate
1010: Solid-state imaging device
11000: Endoscopic surgery system
12000: Vehicle control system

The invention claimed is:
1. A solid-state imaging element comprising:
a first pixel circuit and a second pixel circuit, each including a first transistor, a second transistor and a photoelectric converter that performs photoelectric conversion on received light to generate a pixel signal, the first transistor being configured to amplify the pixel signal generated by the photoelectric converter the second transistor being configured to receive a reference signal from a reference signal generator, and
a third transistor that is shared by the first pixel circuit and the second pixel circuit, the third transistor being configured to respectively output bias current to the first transistor and the second transistor of the first and second pixel circuits.
2. The solid-state imaging element according to claim 1, wherein
sources of the first transistor and the second transistor are connected with a drain of the third transistor, and
the reference signal generator is connected with a gate of the second transistor, and a source of the third transistor is connected to a ground.
3. The solid-state imaging element according to claim 2, wherein drains of the first transistor and the second transistor are connected with a current mirror circuit that is distinct from the first and second pixel circuits.
4. The solid-state imaging element according to claim 1, wherein the first transistor, the second transistor, and the third transistor are linearly arranged in this order.
5. The solid-state imaging element according to claim 4, wherein a source of the second transistor and a ground node with which a drain of the third transistor is connected are adjacent to each other.
6. The solid-state imaging element according to claim 1, wherein the first transistor, the second transistor, and the third transistor share a diffusion layer.
7. The solid-state imaging element according to claim 1, wherein the third transistor is shared through routing wiring formed for connecting the first and second pixel circuits.
8. The solid-state imaging element according to claim 1, wherein the first pixel circuit is arranged on a first semiconductor substrate and the second pixel circuit is arranged on a second semiconductor substrate, the first and second semiconductor substrates being laminated in a stacked structure.
9. The solid-state imaging element according to claim 1, further comprising:
a first semiconductor substrate on which at least portions of the first pixel circuit and the second pixel circuit are arranged; and
a second semiconductor substrate on which the third transistor is arranged.
10. The solid-state imaging element according to claim 1, wherein the first transistor, the second transistor, and the third transistor are arranged on a first substrate different from a second substrate on which the photoelectric converter is arranged.
11. A solid-state imaging device comprising:
a solid-state imaging element according to claim 1; and
an optical system configured to guide an incident light from a subject to the solid-state imaging element.
12. Electronic equipment comprising solid-state imaging device according to claim 11.
13. The solid-state imaging device according to claim 11, wherein
sources of the first transistor and the second transistor are connected with a drain of the third transistor, and
the reference signal generator is connected with a gate of the second transistor, and a source of the third transistor is connected to a ground.
14. The solid-state imaging device according to claim 13, wherein drains of the first transistor and the second transistor are connected with a current mirror circuit that is separate and distinct from the first and second pixel circuits.
15. The solid-state imaging device according to claim 11, wherein the first transistor, the second transistor, and the third transistor are linearly arranged in this order.
16. The solid-state imaging device according to claim 15, wherein a source of the second transistor and a ground node with which a drain of the third transistor is connected are adjacent to each other.
17. The solid-state imaging device according to claim 11, wherein the first transistor, the second transistor, and the third transistor share a diffusion layer.
18. The solid-state imaging device according to claim 11, wherein the third transistor is shared through routing wiring formed for connecting the first and second pixel circuits.
19. The solid-state imaging device according to claim 11, wherein the first pixel circuit is arranged on a first semiconductor substrate and the second pixel circuit is arranged on a second semiconductor substrate, the first and second semiconductor substrates being laminated in a stacked structure.
20. The solid-state imaging device according to claim 11, wherein the first transistor, the second transistor, and the third transistor are arranged on a first substrate different from a second substrate on which the photoelectric converter is arranged.

21. The solid-state imaging device according to claim 1, further comprising:
- a first semiconductor substrate on which at least portions of the first pixel circuit and the second pixel circuit are arranged; and
- a second semiconductor substrate on which the third transistor is arranged.

* * * * *